United States Patent
Kallmyer

(10) Patent No.: US 11,160,985 B2
(45) Date of Patent: Nov. 2, 2021

(54) MEDICAL DEVICE WITH MULTIPLE CHANNEL INDEPENDENT RATE CONTROL

(71) Applicant: Medtronic, Inc., Minneapolis, MN (US)

(72) Inventor: Todd A. Kallmyer, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

(21) Appl. No.: 16/200,222

(22) Filed: Nov. 26, 2018

(65) Prior Publication Data
US 2019/0091477 A1 Mar. 28, 2019

Related U.S. Application Data

(63) Continuation of application No. 12/694,830, filed on Jan. 27, 2010, now Pat. No. 10,137,304.

(51) Int. Cl.
*A61N 1/36* (2006.01)
*A61N 1/05* (2006.01)

(52) U.S. Cl.
CPC ....... *A61N 1/36171* (2013.01); *A61N 1/0553* (2013.01); *A61N 1/0534* (2013.01)

(58) Field of Classification Search
CPC . A61N 1/0553; A61N 1/0534; A61N 1/36171
See application file for complete search history.

(56) References Cited

U.S. PATENT DOCUMENTS

| | | | |
|---|---|---|---|
| 3,893,463 | A | 7/1975 | Williams |
| 4,398,537 | A | 8/1983 | Holmbo |
| 4,401,119 | A | 8/1983 | Herpers |
| 5,324,317 | A | 6/1994 | Reiss |
| 5,470,342 | A | 11/1995 | Mann et al. |

(Continued)

FOREIGN PATENT DOCUMENTS

| | | |
|---|---|---|
| GB | 2091109 A | 7/1982 |
| GB | 2123698 A | 2/1984 |

(Continued)

OTHER PUBLICATIONS

Notification of Transmittal of the International Search Report and the Written Opinion of the International Searching Authority for Corresponding Patent Application Np. PCT/US10/055558, dated Feb. 8, 2011, 10 pages.

(Continued)

*Primary Examiner* — Alyssa M Alter
(74) *Attorney, Agent, or Firm* — Shumaker & Sieffert, P.A.

(57) ABSTRACT

Techniques are described in this disclosure for delivering electrical stimulation therapy to a patient over multiple channels, with independent rate control for each channel, using a single stimulation generator. In one example, the disclosure describes a method for delivering electrical stimulation therapy to a patient that includes delivering first electrical stimulation pulses at a first programmed rate on a first channel using a stimulation generator, and delivering second electrical stimulation pulses at a second programmed rate on a second channel using the stimulation generator, the second programmed rate being different than the first programmed rate, and the second programmed rate being independent of the first programmed rate.

27 Claims, 10 Drawing Sheets

(56) References Cited

U.S. PATENT DOCUMENTS

| | | |
|---|---|---|
| 6,052,624 A | 4/2000 | Mann |
| 6,393,325 B1 | 5/2002 | Mann et al. |
| 6,516,227 B1 | 2/2003 | Meadows et al. |
| 6,587,724 B2 | 7/2003 | Mann |
| 6,609,031 B1 | 8/2003 | Law et al. |
| 6,731,986 B2 | 5/2004 | Mann |
| 6,909,917 B2 | 6/2005 | Woods et al. |
| 7,076,301 B1 | 7/2006 | Kroll et al. |
| 7,519,431 B2 | 4/2009 | Goetz et al. |
| 10,137,304 B2 | 11/2018 | Kallmyer |
| 2005/0113875 A1* | 5/2005 | Ternes ................. A61N 1/3702 607/9 |
| 2006/0224199 A1 | 10/2006 | Zeijlemaker |
| 2006/0229687 A1 | 10/2006 | Goetz et al. |
| 2006/0247718 A1 | 11/2006 | Starkebaum |
| 2006/0259099 A1 | 11/2006 | Goetz et al. |
| 2009/0048643 A1 | 2/2009 | Erickson et al. |

FOREIGN PATENT DOCUMENTS

| | | |
|---|---|---|
| WO | 9641655 A1 | 12/1996 |
| WO | 03090857 | 11/2003 |

OTHER PUBLICATIONS

Prosecution History from U.S. Appl. No. 12/694,830, dated May 15, 2012, through Jul. 12, 2018, 208 pp.

* cited by examiner

MEDICAL DEVICE WITH MULTIPLE CHANNEL INDEPENDENT RATE CONTROL

This application is a continuation of U.S. patent application Ser. No. 12/694,830, filed Jan. 27, 2010 and entitled "MEDICAL DEVICE WITH MULTIPLE CHANNEL INDEPENDENT RATE CONTROL," the entire content of which is incorporated herein by reference.

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device ("stimulator" or "electrical stimulator") may be fully implanted within the patient. For example, a stimulator may include an implantable electrical stimulation generator and one or more implantable leads carrying electrodes. In some cases, implantable electrodes may be coupled to an external electrical stimulation generator via one or more percutaneous leads or fully implanted leads.

Stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a current or voltage pulse amplitude, pulse width and pulse rate. A set of parameter values may be referred to as a stimulation program. A program group may include multiple programs. Multiple programs in a program group may be delivered on a simultaneous, time-interleaved, or overlapping basis.

SUMMARY

This disclosure describes techniques for delivering electrical stimulation therapy to a patient over multiple channels, with independent rate control for each channel, using a single stimulation generator. A stimulator, such as an implantable stimulator or external medical device for delivering deep brain stimulation (DBS), cortical stimulation (CS), spinal cord stimulation (SCS), peripheral nerve stimulation (PNS), peripheral nerve field stimulation (PNFS), pelvic floor stimulation, gastric stimulation, or other neurostimulation or cardiac stimulation, includes a stimulation generator that is shared between the multiple channels. The rate at which electrical stimulation, e.g., pulses, is delivered by the stimulation generator may be programmed for each of the channels. The rate at which electrical stimulation therapy is delivered over each of the channels may be varied independently of the other channels. The stimulator adaptively delivers the stimulation therapy over the multiple channels so as to maintain the programmed rates for each of the channels. The stimulator may also adjust recharge signals for the electrical stimulation to allow for a selectable trade-off between fidelity to programmed rate and amplitude.

The stimulator may adaptively deliver electrical stimulation at independent rates and adjust recharge signals associated with the stimulation using independent rate counters and queues in order to provide multi-channel rate control using a single stimulation generator. Each channel may be associated with a downcounter ("counter"), for example, and a backlog queue. Each counter may track the programmed rate at which stimulation is to be delivered for a corresponding channel. The stimulator may increment a queue associated with a counter when the counter reaches zero, i.e., triggers a rate interval, and may decrement the queue when a pulse is delivered on the corresponding channel. Accordingly, each queue may track the pulse backlog for the corresponding channel. The stimulator may deliver stimulation, using a single stimulation generator, over multiple channels based on the population of the queues.

In particular, the stimulator may deliver electrical stimulation to a patient based on rules stored in memory. The stimulation rules may govern the prioritization for delivering backlogged pulses. Because independent rate control is provided for each channel, the channels may deliver stimulation at different rates. So, a queue associated with a higher-rate channel may populate, or fill, faster than a queue associated with a lower-rate channel. The queue (or backlog) associated with the higher-rate channel increases as a result of the higher-rate channel pulse delaying while stimulation is delivered on the lower-rate channel. When the queue of the higher-rate channel exceeds the queue of the lower-rate channel, the higher-rate channel may deliver two consecutive pulses to "catch up" to its programmed rate. In some example implementations, the stimulator may use rate blanking to avoid delivering consecutive pulses on a channel, e.g., the higher-rate channel, at an unnecessarily high rate. The stimulator may also adaptively adjust one or both of a recharge interval, and recharge amplitude associated with the recharge signal.

In one example, the disclosure is directed to a method for delivering electrical stimulation therapy to a patient. The method comprises delivering a first plurality of electrical stimulation pulses at a first programmed rate on a first channel using a stimulation generator, and delivering a second plurality of electrical stimulation pulses at a second programmed rate on a second channel using the stimulation generator, wherein the second programmed rate is different than the first programmed rate, and wherein the second programmed rate is independent of the first programmed rate.

In another example, the disclosure is directed to a device comprising a stimulation generator, and a processor configured to execute instructions that cause the stimulation generator to deliver a first plurality of electrical stimulation pulses at a first programmed rate on a first channel using the stimulation generator, and deliver a second plurality of electrical stimulation pulses at a second programmed rate on a second channel using the stimulation generator, wherein the second programmed rate is different than the first programmed rate, and wherein the second programmed rate is independent of the first programmed rate.

In another example, the disclosure is directed to a system comprising an array of implantable electrodes and an implantable medical device coupled to the array. The device comprises a stimulation generator, and a processor configured to execute instructions that cause the stimulation generator to deliver a first plurality of electrical stimulation pulses at a first programmed rate on a first channel using the stimulation generator, and deliver a second plurality of electrical stimulation pulses at a second programmed rate on a second channel using the stimulation generator, wherein the second programmed rate is different than the first programmed rate, and wherein the second programmed rate is independent of the first programmed rate.

The details of one or more aspects of the disclosure are set forth in the accompanying drawings and the description below. Other features, objects, and advantages of the invention will be apparent from the description and drawings, and from the claims.

DETAILED DESCRIPTION

Figure 1:
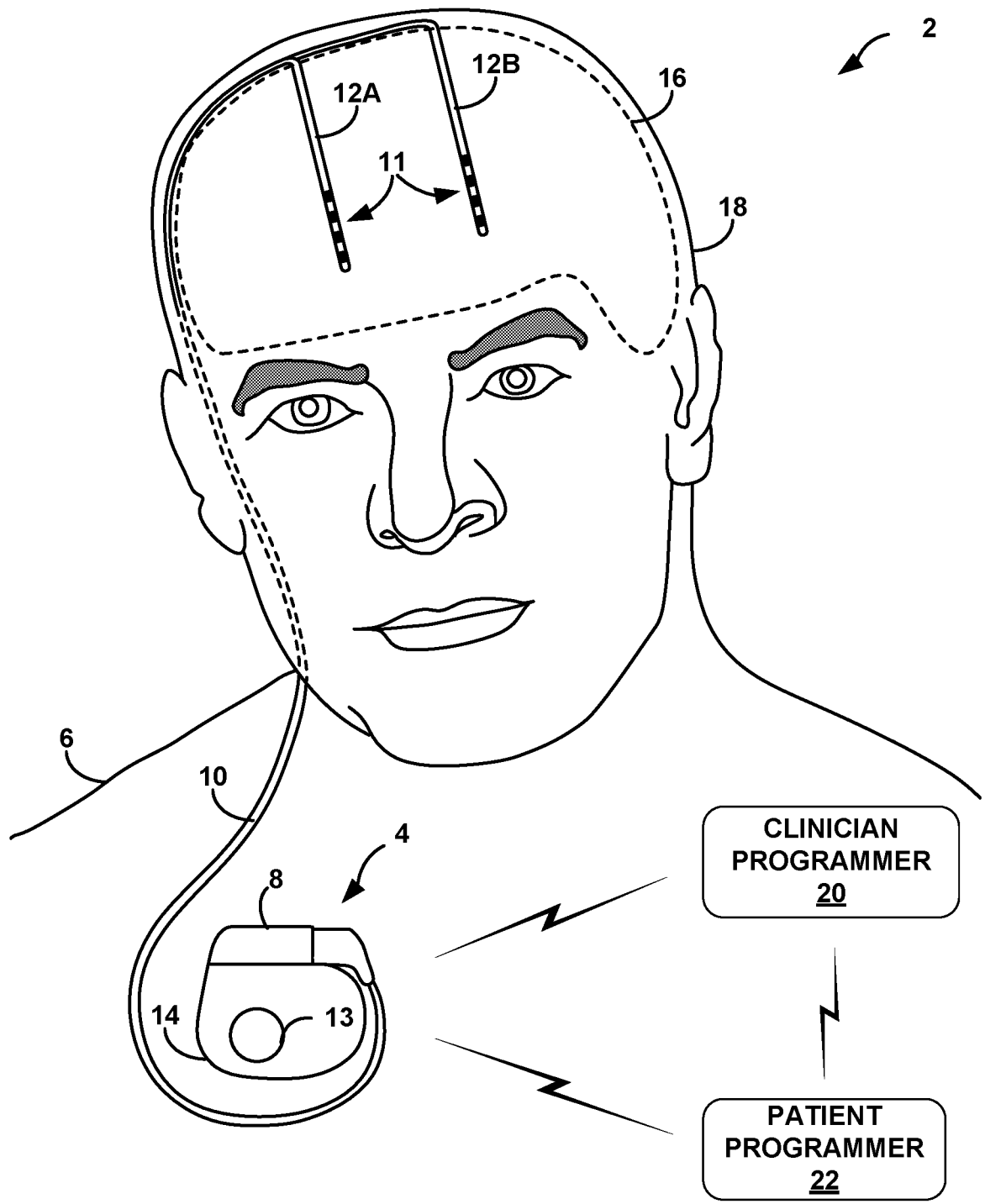
FIG. 1 is a conceptual diagram illustrating an example system that includes an implantable stimulator for delivering electrical stimulation to a patient at independent rates on different channels in accordance with techniques described in this disclosure.

Techniques are described in this disclosure for delivering electrical stimulation therapy to a patient over multiple channels, with independent rate control for each channel, using a single stimulation generator. The single stimulation generator may be a device which, for two or more channels, creates a suitable energy supply, such as a voltage stored on a capacitor, and controls delivery of that energy supply, e.g., by regulating amplitude and pulse width. The single stimulation generator may also regulate recharge, i.e., reverse flow, energy amplitude and pulse width, to create charge-balance.

A stimulator, such as an implantable stimulator or external medical device for delivering deep brain stimulation (DBS), cortical stimulation (CS), spinal cord stimulation (SC S), peripheral nerve stimulation (PNS), peripheral nerve field stimulation (PNFS), pelvic floor stimulation, gastric stimulation, or other neurostimulation or cardiac stimulation, includes a stimulation generator that is shared between the multiple channels. The stimulator may deliver electrical stimulation to a patient based on rules stored in memory. Independent rate control may refer to the ability to control the electrical stimulation rate of each channel without reference to, or in any way restricted by, the electrical stimulation rates of the other channels using the same stimulation generator. For example, in a two channel implementation using independent rate control, the programmed stimulation rate (M) of a second channel need not be a multiple, or integerM/integerN, of the programmed stimulation rate (N) of the first channel.

Generally, if the programmed rates for the multiple channels are different from one another, the rules may be configured to deliver the electrical stimulation pulses with the most even spacing of pulses possible in an attempt to mimic the programmed rates. An example set of rules may stipulate that a pulse is delivered when there is a queue with some population in it, another channel is not delivering a stimulation pulse or recharge signal, and the channel that wants to deliver the pulse has waited long enough since its last pulse. Generally, while the stimulator delivers electrical stimulation and the associated recharge signal on a channel, the stimulator blanks the other channels.

The stimulator may also adjust, according to another set of rules stored in memory, a recharge signal associated with electrical stimulation delivered on multiple channels. After an electrical stimulation signal is delivered, a corresponding recharge signal, e.g., a pulse or continuous waveform, is delivered on the same channel to recover charge in order to deliver approximately zero net charge to the patient. The stimulator may adjust the interval of the recharge signal, the amplitude of the recharge signal, or both. For example, the stimulator may adjust the recharge interval within predefined limits, e.g., a maximum and minimum value, to automatically allow for full charge balance or to avoid amplitude sag. As another example, the stimulator may adjust the amplitude of a recharge pulse to allow for full charge balance or to avoid amplitude sag. Specifically, the stimulator may increase the recharge amplitude when the recharge interval is shortened.

Amplitude sag may occur when a stimulator is not able to fully recharge before delivering the next electrical stimulation pulse. Thus, the next stimulation pulse that the stimulator delivers is not delivered with the programmed pulse amplitude, i.e., the amplitude of the next stimulation pulse "sags." On the other hand, when charge balance or amplitude sag is not a factor, such as when there is sufficient time between pulses for a "full" recharge interval, the stimulator may extend the recharge interval. Because faster recharge requires a higher generated voltage, extending the recharge interval may deplete the power source less rapidly and, therefore, may extend the life of the power supply.

The stimulator may adjust the recharge signal for each channel, and each channel may be programmed with a default recharge interval and amplitude. The rules, however, may allow one or both of the recharge interval and amplitude to be adjusted within certain limits based on the queues. For example, the recharge interval may be increased and decreased by a fixed predetermined amount within a maximum and minimum (threshold) value. As another example, the recharge interval may be selected from a plurality of values that range between the minimum and maximum value.

As one example, a default recharge interval may be approximately 3.9 milliseconds (ms). The recharge interval may be increased and decreased by a fixed predetermined amount of approximately 1.95 ms and have a maximum value of 7.8 ms and a minimum value of 1.95 ms. In some examples, the recharge rules may adjust the recharge interval based on the total sum of the queues. As an example, the stimulator may increase the recharge interval when the sum of the queues is "1" and may decrease the recharge interval when the sum of the queues is more than "2." The stimulator may neither increase nor decrease the recharge interval when the sum of the queues is equal to "2." In some examples, when both channels are rate limit waiting, the stimulator may allow the recharge signal to extend past the set recharge interval. A channel is "rate limit waiting" when the channel is inactive, but not available for delivering stimulation because the channel has not waited long enough before delivering another stimulation pulse. Accordingly, the recharge signal may be allowed to extend to the maximum value when the channels are rate limit waiting.

The stimulator may be implemented in a medical device that is implanted in the body of a patient or a medical device external to the body of the patient. The stimulator may deliver stimulation in the form of voltage or current pulses. In one example, the stimulation generator may be included in an implantable stimulator for delivering deep brain stimulation (DBS) or cortical stimulation (CS) to a patient. In particular, such an implantable stimulator may be coupled to leads implanted within right and left hemispheres of the brain and may deliver stimulation to each hemisphere at independent rates. In other examples, the stimulation generator may be implemented in an implantable stimulator implanted within the patient for delivering spinal cord stimulation (SCS) to the patient or other therapies, such as peripheral nerve stimulation (PNS), peripheral nerve field stimulation (PNFS), pelvic floor stimulation, gastric stimulation, or other neurostimulation or cardiac stimulation. As another example, the stimulator may be an implantable pacemaker, cardioverter, defibrillator, or external medical device that provides cardiac stimulation that shares a stimulation generator between multiple channels.

FIG. 1 is a conceptual diagram illustrating an example system 2 that may be used to deliver electrical stimulation therapy to patient 6. Patient 6 ordinarily, but not necessarily, will be a human. Generally, therapy system 2 includes an implantable stimulator 4, also referred to in this disclosure as implantable medical device (IMD) 4, that delivers electrical stimulation therapy to patient 6 via one or more implantable electrodes. In accordance with the techniques of this disclosure, IMD 4 may provide electrical stimulation therapy to patient 6 using multi-channel rate control and adjustable recharge intervals. IMD 4 may include a single stimulation circuit, or stimulation generator, for generating and delivering electrical stimulation pulses and corresponding recharge pulses having recharge intervals over multiple channels. A physician may program the pulse rate for each channel independently of the other channels. IMD 4 may adaptively deliver the stimulation pulses on the multiple channels so as to maintain the programmed rates for each of the channels. IMD 4 may also automatically adjust the recharge signal associated with the stimulation pulse to provide a selectable trade-off between fidelity to the programmed rate and programmed amplitude. Specifically, IMD 4 may automatically adjust one, or both of, the time interval and amplitude of the recharge signal.

Various parameters of the stimulation pulses may be defined by a stimulation program. The stimulation pulses may be delivered substantially continuously or in bursts, segments, or patterns, and may be delivered alone or in combination with pulses defined by one or more other stimulation programs. As indicated above, stimulation pulses may be delivered on two or more channels with each channel delivering pulses according to a different programmed rate. Although FIG. 1 shows a fully implantable stimulator 4, as mentioned above, techniques described in this disclosure may be applied to external stimulators having electrodes deployed via percutaneously implantable leads. In addition, in some cases, implantable electrodes may be deployed on a leadless stimulator.

In the example illustrated in FIG. 1, implantable stimulator 4 is implanted within a subcutaneous pocket in a clavicle region of patient 6. Stimulator 4 generates programmable electrical stimulation, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes, for example. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

Additionally, the electrodes carried on leads 12A and 12B may alone or in combination be associated with different channels for delivering electrical stimulation. For example, the electrodes carried on leads 12A may be selected to deliver electrical stimulation according to one set of parameters on a first channel and the electrodes carried on lead 12B may be selected to deliver electrical stimulation according to another set of stimulation parameters on a second channel. Accordingly, implantable stimulator 4 may deliver electrical stimulation at one programmed rate to the right hemisphere of the brain of patient 6 via electrodes on lead 12A and deliver electrical stimulation at another programmed rate to the left hemisphere of the brain of patient 6 via electrodes on lead 12B.

FIG. 1 further depicts an example housing, or can, electrode 13. Housing electrode 13 may be formed integrally with an outer surface of hermetically-sealed housing 14 of implantable stimulator 4, also referred to in this disclosure as an implantable medical device (IMD), or otherwise coupled to housing 14. In some examples, housing electrode 13 is defined by an uninsulated portion of an outward facing portion of housing 14 of implantable stimulator 4. Other divisions between insulated and uninsulated portions of housing 14 may be employed to define two or more housing electrodes, which may be referred to as case or can electrodes. In some examples, housing electrode 13 comprises substantially all of housing 14, or a portion of the housing 14. Housing electrode 13 typically may comprise an anode, although the housing electrode could be formed as a cathode in some cases.

A proximal end of lead 10 may be both electrically and mechanically coupled to header 8 on implantable stimulator 4 either directly or indirectly via a lead extension. Conductors in the lead body may electrically connect stimulation electrodes located on leads 12A and 12B to implantable stimulator 4. In the example of FIG. 1, lead 10 traverses from the implant site of implantable stimulator 4 along the neck of patient 6 to cranium 18 of patient 6 to access brain 16. Leads 12A and 12B are implanted within the right and left hemispheres, respectively, in order to deliver electrical stimulation to one or more regions of brain 16, which may be selected based on patient condition or disorder.

Implantable stimulator 4 may deliver, for example, deep brain stimulation (DBS) or cortical stimulation (CS) therapy to patient 6 via the electrodes carried by, e.g., located on, leads 12A and 12B to treat any of a variety of neurological disorders or diseases. Example neurological disorders may include depression, dementia, obsessive-compulsive disorder and movement disorders, such as Parkinson's disease, spasticity, epilepsy, and dystonia. In some examples, stimulator 4 may deliver DBS to treat epilepsy in combination with other DBS. DBS also may be useful for treating other patient conditions, such as migraines and obesity. However, the disclosure is not limited to the configuration of lead 10 shown in FIG. 1, or to the delivery of DBS or CS therapy.

Leads 12A and 12B may be implanted within a desired location of brain 16 through respective holes in cranium 18. Leads 12A and 12B may be placed at any location within brain 16 such that the electrodes located on leads 12A and 12B are capable of providing electrical stimulation to targeted tissue during treatment. Example locations for leads 12A and 12B within brain 16 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, leads 12A and 12B may be implanted to provide stimulation to the visual cortex of brain 16 in order to reduce or eliminate migraine headaches afflicting patient 6. However, the target therapy delivery site may depend upon the patient condition or disorder being treated.

The electrodes of leads 12A and 12B are shown as ring electrodes. Ring electrodes are commonly used in DBS applications because they are simple to program and are capable of delivering an electrical field to any tissue adjacent to leads 12A and 12B. In other implementations, the electrodes of leads 12A and 12B may have different configurations. For example, the electrodes of leads 12A and 12B may have a complex electrode array geometry that is capable of producing shaped electrical fields. The complex electrode array geometry may include multiple electrodes (e.g., partial ring or segmented electrodes) around the perimeter of each leads 12A and 12B, rather than one ring electrode. In this manner, electrical stimulation may be directed in a specific direction from leads 12A and 12B to enhance therapy efficacy and reduce possible adverse side effects from stimulating a large volume of tissue. In alternative examples, leads 12A and 12B may have shapes other than elongated cylinders as shown in FIG. 1. For example, leads 12A and 12B may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation pulse parameters, e.g., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, current or voltage pulse amplitude (i.e., level), pulse width, pulse shape, and pulse rate. Patient 6 may also select a program, e.g., from among a plurality of stored programs, as the present program to control delivery of stimulation by implantable stimulator 4, or select different program groups.

In some examples, stimulator 4 delivers stimulation according to a group of programs at a given time. Each program of such a program group may include respective values for each of a plurality of therapy parameters, such as respective values for each of pulse level (i.e., amplitude), pulse width, pulse shape, pulse rate and electrode configuration. Stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Stimulator 4 enables the pulse rate for each of the programmed rates to be selected independently of each other. Patient programmer 22 may be used to adjust stimulation parameters of one or more programs of a program group, and select a program group, e.g., from among a plurality of stored program groups, as the current program group to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art. Clinician programmer 20 and patient programmer 22 also may communicate with each other, or other devices, using any of a variety of local wireless communication techniques, such as RF communication according to the 802.11 or Bluetooth specification sets, infrared communication, e.g., according to the IrDA standard, or other standard or proprietary telemetry protocols.

Clinician programmer 20 and patient programmer 22 may each include a transceiver to permit bi-directional communication with stimulator 4. Programmers 20, 22 may also communicate with another programming or computing device via exchange of removable media, such as magnetic or optical disks, or memory cards or sticks. Further, programmers 20, 22 may communicate with implantable stimulator 4 and other programming devices via remote telemetry techniques known in the art, communicating via a local area network (LAN), wide area network (WAN), public switched telephone network (PSTN), or cellular telephone network, for example.

Generally, stimulator 4 may include a single stimulation generator and be configured to deliver electrical stimulation pulses to patient 6 over two or more channels. A clinician or physician may, using clinician programmer 20, define the pulse rate and other stimulation parameters for each of the channels. In particular, the clinician or physician may define the pulse rate for each of the channels independent of the other channels. For example, pulses on a first channel may be programmed to be delivered at a first rate and pulses on a second channel may be programmed to be delivered at a second rate that is different than, and not restricted by, the first programmed rate. As will be described in more detail below, stimulator 4 may adaptively deliver the electrical stimulation pulses in order to maintain the programmed rates. In addition, stimulator 4 may automatically adjust a recharge interval of a recharge pulse delivered following each corresponding electrical stimulation pulse.

According to the techniques of this disclosure, stimulator 4 may use a rate counter and queue, for example, for each channel to adaptively deliver the electrical stimulation pulses and adjust recharge intervals associated with the electrical stimulation pulses. The counters may track the programmed pulse rate for the corresponding channel. Stimulator 4 may increment a queue when the corresponding rate counter triggers a rate interval, e.g., reaches zero (indicating that, according to the programmed rate, it is time to provide a stimulation pulse), and decrement the queue when a stimulation pulse is delivered on the corresponding channel. Accordingly, each queue tracks the pulse backlog for the corresponding channel and stimulator 4 delivers stimulation pulses over the channels based on the queues. In particular, stimulator 4 may deliver stimulation pulses based on rules, e.g., stimulation rules, stored in memory.

The stimulation rules may govern the prioritization for delivering backlogged pulses. Generally, a queue for a higher-rate channel may populate faster than a queue for a lower-rate channel. The queue, or backlog, for the higher-rate channel grows as a result of pulse delaying while stimulator 4 delivers stimulation on the lower-rate channel. In order to maintain the programmed rates for each channel, the higher-rate channel is allowed to "catch up" to its programmed rate by delivering consecutive pulses on the higher-rate channel. When delivering the consecutive pulses on the higher-rate channel, the lower-rate channel may prevent a pulse from being delivered, or "pulse delay." The higher-rate channel may, for example, be allowed to "catch up" to its programmed rate when the queue associated with the higher-rate channel is greater than the queue associated with the lower-rate channel.

In some examples, stimulator 4 may use rate blanking to avoid delivering consecutive pulses on a channel, e.g., the higher-rate channel, at an unnecessarily high rate. Rate blanking refers to requiring a channel to wait a predetermined period of time before delivering another pulse on the same channel. An example rate blanking interval may be equal to the programmed rate interval. The rate blanking interval for a channel is triggered when a pulse is delivered on the channel. In some examples, however, stimulator 4 may adjust the rate blanking interval. For example, stimulator 4 may decrease the time period of the rate blanking interval when the higher-rate channel needs to "catch up." Decreasing the rate blanking interval allows the higher-rate channel to "catch up" more quickly.

In general, the stimulation rules may allow stimulator 4 to deliver multiple electrical stimulation pulses having different programmed rates with the most even spacing possible. Example stimulation rules may select as the active channel, i.e., the channel to deliver the pulse, the channel with the largest associated queue. The largest queue may be determined by comparing the values of the queues, e.g., "0," "1," and "2." With reference to this disclosure, the largest queue is the queue with the largest backlog of pulses. Example stimulation rules may also include that a pulse is delivered when there is a queue with some population in it, another channel is not delivering a pulse or recharging, and that the active channel has waited long enough since its last pulse (that is, the rate blanking interval for the channel has expired). Generally, the channel that is not active, e.g., the inactive channel, is blanked while stimulation is delivered on the active channel. In some specific implantations, stimulator 4 may support a rate of approximately 182 Hertz (Hz) on one or both of the channels at a pulse width of approximately 450 µs.

Stimulator 4 may also adjust, according to another set of rules stored in memory, a recharge interval for a recharge signal associated with electrical stimulation delivered on the multiple channels. Similar to the stimulation rules, the recharge rules may determine how the recharge signals are adjusted based on the queues. Stimulator 4 may adjust the recharge interval associated with recharge signal, the amplitude of the recharge signal, or both.

A recharge signal may comprise one or more recharge pulses, or may be a continuous waveform. A recharge pulse, as referred to in this disclosure, is an electrical pulse that is delivered substantially immediately following an electrical stimulation pulse. Similarly, a recharge waveform is a continuous electrical waveform delivered substantially immediately following an electrical stimulation pulse. The recharge pulse or waveform is generated with a charge level approximately equal to that of the corresponding electrical stimulation pulse, and is delivered on the same channel as the electrical stimulation pulse, but in an opposite direction as the delivered stimulation pulse, so that approximately zero net charge is delivered to the patient over the channel. The recharge signal, i.e., recharge pulse or recharge waveform, is generally a subthreshold signal, e.g., below perception threshold that does not stimulate a nerve or muscle tissue of the patient.

The recharge interval generally refers to the time period over which the recharge signal is delivered. With respect to a recharge pulse, decreasing the recharge interval, i.e., decreasing the time period over which the recharge pulse is delivered, may decrease the amount of time that stimulator 4 can recharge. Decreasing the recharge interval in this way may lead to amplitude sag, or insufficient time to charge-balance. Amplitude sag may occur, for example, when stimulator 4 is not able to fully recharge before delivering the next electrical stimulation pulse. For example, in one high-energy application, the voltage amplitude may sag from 10 volts to 7.5 volts (V). However, decreasing the recharge interval may be advantageous when the higher-rate channel is backlogged and needs to "catch up" to its programmed rate. Consequently, there is a tradeoff between fidelity to the programmed rate and pulse amplitude. For this reason, extending the recharge interval may be advantageous because doing so may deplete the power source less rapidly and, therefore, may extend the life of the stimulator.

In some examples, stimulator 4 may adjust, i.e., increase and decrease, the amplitude of the recharge signal. As one example, stimulator 4 may increase the amplitude of the recharge pulse when the recharge interval is shortened. In such an example, the recharge amplitude may correspond to a predetermined voltage threshold. Accordingly, increasing the recharge amplitude may involve increasing the voltage threshold. Thus, a relationship may be defined between the recharge interval and recharge amplitude/voltage threshold. In any case, increasing the recharge amplitude may reduce the efficiency and, therefore, decrease the battery life of stimulator 4. However, at the same time, this may allow stimulator 4 to deliver stimulation at the programmed rate and amplitude.

Stimulator 4 may adjust a recharge signal, i.e., one or both of a recharge interval and recharge amplitude, for each of the channels according to the stimulation rules. The stimulation rules may automatically adjust the recharge signals to optimize the tradeoff between fidelity to programmed rate and amplitude sag or charge balance. In some examples, stimulator 4 may adjust the recharge interval to be as large as possible while maintaining the programmed rate.

In some examples, the recharge rules may adjust the recharge signal based on the sum of the values in each queue. In particular, the sum of the values in each queue may be compared to a predetermined value and, based on the comparison, the recharge interval, recharge amplitude, or both, may be increased, decreased, or maintained at its current value. As one specific example, in a two channel configuration, the stimulator may increase the recharge interval when the sum of the value in the queue associated with the first channel and the value of the queue associated with the second channel equals "1." The stimulator in the two channel configuration may decrease the recharge interval when the sum of the value in the queue associated with the first channel and the value of the queue associated with the second channel is greater than "2." In the two channel configuration, the stimulator may maintain, i.e., neither increase nor decrease, the present recharge interval when the sum the value in the queue associated with the first channel and the value of the queue associated with the second channel is equal to "2." In some example two channel configurations, when both channels are rate limit waiting for a period of time, the stimulator may allow the recharge interval for each of the channels to extend to the maximum value. Channels are "rate limit waiting" when the channels are inactive, but not available for delivering stimulation because rate blanking intervals for the channels have not expired.

In some examples, stimulator 4 may adjust the recharge intervals within predefined limits, e.g., within predetermined maximum and minimum values. In one example, stimulator 4 may increase and decrease the recharge interval by a predetermined amount within the predetermined limits. As another example, the recharge interval may be selected from a plurality of predetermined values that range between the minimum and maximum value.

In one example implementation, a recharge interval may be programmed with a default value of approximately 3.9 milliseconds (ms). Stimulator 4 may increase and decrease the recharge interval by a fixed predetermined amount of approximately 1.95 ms and have a maximum value of 7.8 ms and a minimum value of 1.95 ms. So, if stimulator 4 increases the recharge interval twice by the fixed predetermined amount of 1.95 ms, beginning with a recharge interval of 3.9 ms, the recharge interval will be 7.8 ms.

With respect to FIG. 1, combinations of the electrodes carried on leads 12A and 12B may be selected by the clinician as different "channels" for delivering electrical stimulation. For example, a clinician may program stimulator 4 to deliver electrical stimulation at one rate using electrodes on lead 12A and at a different rate using electrodes on lead 12B. In another example, a clinician may program stimulator 4 to deliver electrical stimulation at one rate, on one channel, using one or more electrodes on lead 12A and at a different rate, on a different channel, using one or more different electrodes on lead 12A. In other examples, a first combination of electrodes on leads 12A and 12B may deliver stimulation at a first rate on one channel and a second combination of electrodes on leads 12A and 12B may deliver stimulation at a second rate on another channel.

Various parameters of the stimulation pulses may also be defined by a stimulation program. For example, a stimulation program may define the pulse rate, current or voltage amplitude, pulse width, pulse shape, program duration, and electrode configuration, e.g., electrode combination and polarity. Again, an electrode configuration is referred to in this disclosure as a channel for the purposes of simplicity.

Figure 2:
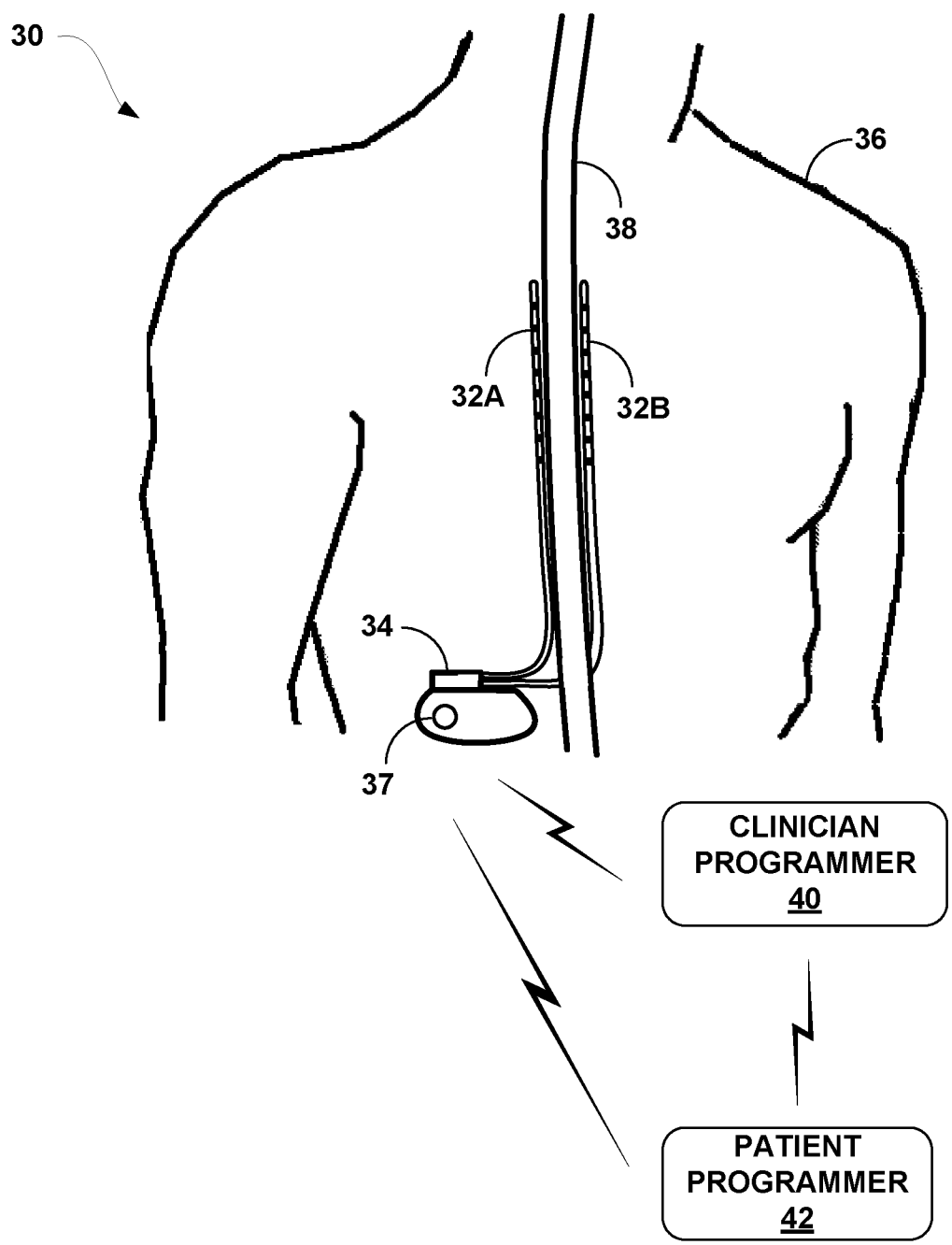
FIG. 2 is a conceptual diagram illustrating another example therapy system that includes an implantable stimulator coupled to implantable stimulation leads.

FIG. 2 is a conceptual diagram illustrating a system 30 that delivers electrical stimulation therapy to spinal cord 38 of patient 36. Like FIG. 1, FIG. 2 represents another example of an electrical stimulation system that may support stimulation techniques described in this disclosure. In the example of FIG. 2, system 30 is configured to deliver stimulation therapy from implantable stimulator 34 to spinal cord 38 of patient 36 via a combination of one or more electrodes (not shown) carried by, e.g., located on, implantable medical leads 32A and 32B (collectively "leads 32") as well as electrodes carried by the housing of implantable stimulator 34, e.g., housing electrode 37. Other electrical stimulation systems may be configured to deliver electrical stimulation therapy to gastrointestinal organs, pelvic nerves or muscle, peripheral nerves, or other stimulation sites.

System 30 and, more particularly, implantable stimulator 34 may operate in a manner substantially similar to implantable stimulator 4 (FIG. 1). For example, implantable stimulator 34 may include a single stimulation generator that delivers electrical stimulation pulses over two or more channels. Stimulator 34 may adaptively deliver electrical stimulation pulses to patient 36 over the multiple channels in a way that maintains the programmed rate for each of the channels. Again, the pulse rate for each of the channels may be programmed independently of one another. Stimulator 34 may also adjust recharge intervals for recharge pulses associated with the electrical stimulation pulses.

In the example of FIG. 2, implantable stimulator 34 may deliver electrical stimulation therapy to spinal cord 38 to reduce the amount of pain perceived by patient 36. Generally, stimulator 34 may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The electrical stimulation delivered by implantable stimulator 34 may, for example, take the form of voltage or current pulses defined by pulse amplitude, pulse width, pulse shape, and pulse rate, duration of the stimulation, and electrode configuration or channels, as described above. With respect to FIG. 2, electrical stimulation may be delivered via selected combinations of electrodes, referred to as channels, located on one or both of leads 32 and on the housing of stimulator 34. Stimulation of spinal cord 38 may, for example, prevent pain signals from traveling through the spinal cord and to the brain of patient 36. Patient 36 may perceive the interruption of pain signals as a reduction in pain.

Stimulator 34 may be implanted in patient 36 at a location minimally noticeable to the patient. For SCS, stimulator 34 may be located in the lower abdomen, lower back, or other location to secure the stimulator. Leads 32 are tunneled from stimulator 34 through tissue to reach the target tissue adjacent to spinal cord 38 for stimulation delivery. At the distal ends of leads 32 are one or more electrodes (not shown). Some of the electrodes may be electrode pads on a paddle lead, circular (i.e., ring) electrodes surrounding the body of leads 32, conformable electrodes, cuff electrodes, segmented electrodes, or any other type of electrodes capable of forming unipolar, bipolar, or multi-polar electrode configurations.

In the example of FIG. 2, the distal ends of leads 32 carry electrodes that are placed adjacent to the target tissue of spinal cord 38. The proximal ends of leads 32 may be both electrically and mechanically coupled to implantable stimulator 34 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing.

Implantable stimulator 34 may delivers stimulation to spinal cord 38 to reduce the amount of pain perceived by patient 36. Stimulator 34 may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. Stimulation may be delivered via selected combinations of electrodes (channels) located on one or both of leads 32 and on the housing. Stimulation of spinal cord 38 may, for example, prevent pain signals from traveling through the spinal cord and to the brain of patient 34. Patient 34 may perceive the interruption of pain signals as a reduction in pain.

With reference to FIG. 2, a user, such as a clinician or patient 36, may interact with a user interface of external clinician programmer 40 or patient programmer 42 to program stimulator 34. Programming of stimulator 34 may refer generally to the generation and transfer of commands, programs, or other information to control the operation of the stimulator. For example, each programmer 40, 42 may function in a manner similar to programmers 20, 22, respectively, of FIG. 1 to transmit programs, parameter adjustments, program selections, group selections, or other information to control the operation of stimulator 34, e.g., by wireless telemetry. In general, clinician programmer 40 may support selection and generation of programs by a clinician for use by stimulator 34, whereas patient programmer 42 may support adjustment and selection of such programs by a patient during ordinary use.

Programmers 40, 42, like programmers 20, 22 of FIG. 1, may be configured to communicate with stimulator 34, each other, or other devices via wireless communication. Programmers 40, 42 may communicate, for example, via wireless communication with implantable stimulator 34 using radio frequency (RF) telemetry techniques known in the art. Programmers 40, 42 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmers 40, 42 may also communicate with another programming or computing device via exchange of removable media, such as magnetic or optical disks, or memory cards or sticks. Also, programmers 40, 42 may communicate with implantable stimulator 4 and other programming devices via remote telemetry techniques known in the art, communicating via a local area network (LAN), wide area network (WAN), public switched telephone network (PSTN), or cellular telephone network, for example.

This disclosure is not limited to the configuration of system 2 or system 30, or to the delivery of DBS, CS, or SCS therapy. Rather, it should be recognized that the techniques described in this disclosure may be useful for treating other patient conditions. For example, an implantable or external stimulator may be configured to operate as described in this disclosure for delivering electrical stimulation therapy to patients to relieve a variety of symptoms or conditions, such as chronic pain, tremor, Parkinson's disease, depression, epilepsy, urinary or fecal incontinence, pelvic pain, sexual dysfunction, obesity, migraines, or gastroparesis. An implantable or external stimulator may be configured to deliver electrical stimulation therapy via leads that include electrodes implantable proximate to the spinal cord, pelvic nerves, gastrointestinal organs, peripheral nerves, heart, or within the brain of a patient.

Using the techniques of this disclosure, stimulation therapy may be delivered at independent rates on two or more channels, thereby providing various advantages over other systems. For example, using system 2 shown in FIG. 1 as an example, leads 12A and 12B may be programmed to deliver stimulation therapy at different rates to the right and left hemispheres, respectively. In such an example, delivering stimulation at different rates to different hemispheres of the brain may treat the patient's conditions more fully than would otherwise be possible.

In another example, a stimulator that operates in accordance with the techniques described in this disclosure may be coupled to two or more leads that are each implanted proximate to two different nerves or muscle tissue. Alternatively, each of the leads may be implanted at different locations proximate to the same nerve. In either example, the stimulator may deliver stimulation at different rates on each of the leads. This may allow the stimulator to reduce the amount of pain perceived by the patient or more completely treat the condition of the patient.

Using the techniques of this disclosure, the need to implant multiple stimulators within a patient for treatments that utilize stimulation delivered at different programmed rates may be reduced or eliminated. Using system 2 as an example, stimulator 4 may avoid the need to implant two separate stimulators within patient 6 to deliver electrical stimulation at two independent rates to the left and right hemispheres of the brain. This may reduce the trauma experienced by the patient.

Figure 3:
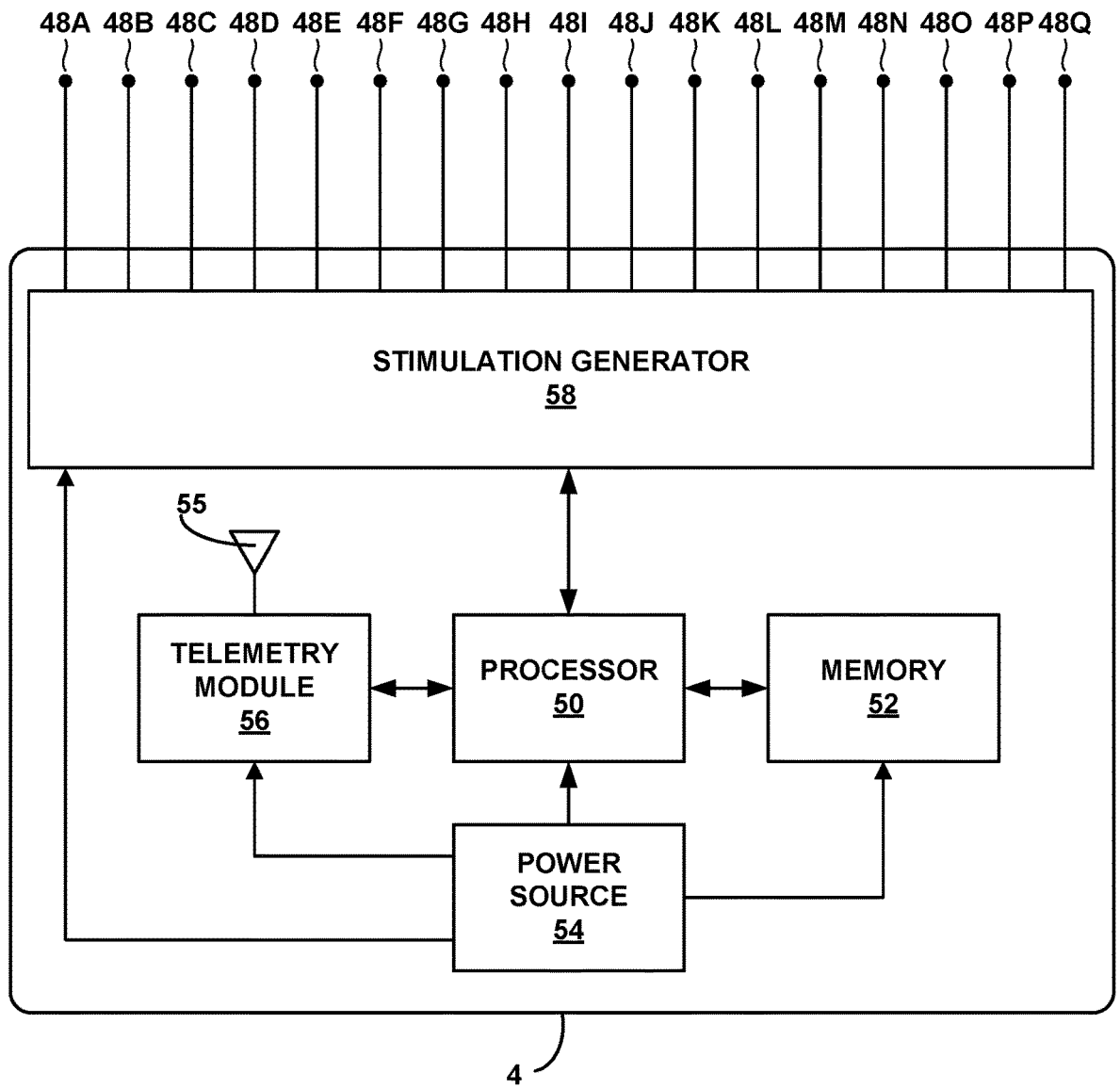
FIG. 3 is a block diagram illustrating various example components of an implantable stimulator.

FIG. 3 is a block diagram illustrating various components of an example implantable stimulator 4 in system 2. Although the components shown in FIG. 3 are described with reference to implantable stimulator 4 (FIG. 1) for purposes of illustration, the same or similar components may also be included within other stimulators, such as implantable stimulator 34 shown in FIG. 2 and used within system 30. Also, in some cases, the components of FIG. 3 may be implemented in an external stimulator. In the example of FIG. 3, implantable stimulator 4 includes processor 50, memory 52, power source 54, telemetry module 56, antenna 57, and a stimulation generator 58. Implantable stimulator 4 is also shown in FIG. 3 coupled to electrodes 48A-Q (collectively "electrodes 48").

Electrodes 48A-48P are implantable and may be deployed on one or more implantable leads. With respect to FIG. 1, lead segments 12A and 12B may carry electrodes 48A-H and electrodes 48I-P, respectively. Accordingly, in some examples, electrodes 48A-H may form a first channel for delivering stimulation to the left hemisphere of the brain and electrodes 48I-P may form a second channel for delivering stimulation to the right hemisphere of the brain. In some cases, one or more additional electrodes, such as electrode 48Q, may be located on or within the housing of implantable stimulator 4, e.g., to provide a common or ground electrode or a housing anode or cathode. With respect to FIG. 2, leads 32A and 32B may carry electrodes 48A-H and electrodes 48I-P, respectively. In the example configurations shown in FIGS. 1 and 2, a lead or lead segment carries eight electrodes to provide a 2×8 electrode configuration (two leads with 8 electrodes each), providing a total of sixteen different electrodes. The leads may be detachable from a housing associated with implantable stimulator 4, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), two leads with four electrodes each (2×4), three leads with four electrodes each (3×4), three leads with eight electrodes each (3×8), three leads with four, eight, and four electrodes, respectively (4-8-4), or other configurations. Different electrodes are selected to form electrode combinations or "channels." Polarities are assigned to the selected electrodes to form electrode configurations.

Electrode 48Q represents one or more electrodes that may be carried on a housing, e.g., can, of implantable stimulator 4. Electrode 48Q may be configured for use in an electrode configuration with selected electrodes among electrodes 48A-48P, which may be located on a lead body of one or more leads, as described above. Electrode 48Q may be formed together on a housing that carries the electrode and houses the components of implantable stimulator 34, such as stimulation generator 58, processor 50, memory 52, telemetry module 56, and power source 54.

Memory 52 may store instructions for execution by processor 50 and stimulation generator 58. Processor 50 may control stimulation generator 58 to deliver electrical stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50 and stimulation generator 58, cause processor 50 and stimulation generator 58 to perform various functions ascribed to processor 50 and stimulation generator 58 in this disclosure.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 4, e.g., controls stimulation generator 58 to deliver stimulation therapy according to a selected program or group of programs retrieved from memory 52. For example, processor 50 may control stimulation generator 58 to deliver electrical signals, e.g., as stimulation therapy and recharge pulses, as pulses or continuous waveforms, with pulse current or voltage amplitudes (i.e., levels), pulse widths (if applicable), and pulse rates specified by one or more stimulation programs. Processor 50 may also control stimulation generator 58 to selectively deliver the stimulation via subsets of electrodes 48, also referred to as "channels" or electrode combinations specified by one or more programs.

Upon selection of a particular program group, processor 50 may control stimulation generator 58 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. In some cases, for a continuous waveform, parameters may include amplitude and frequency. In addition, each program may specify a particular channel for delivery of stimulation, e.g., an electrode configuration in terms of the polarities of the selected electrode combination. The channel or electrode configuration may specify particular electrodes in a single array or multiple arrays, and on a single lead or among multiple leads.

Stimulation generator 58 may include circuitry to generate stimulation pulses and recharge pulses, and circuitry for switching stimulation across different electrode combinations, e.g., in response to control by processor 50. As previously described, stimulation generator 58 may adaptively deliver the electrical stimulation pulses over the two or more selected channels so as to maintain the programmed rates. Additionally, stimulation generator 58 may automatically adjust recharge intervals for corresponding electrical signals.

In accordance with some examples of this disclosure, stimulation generator 58 may utilize a rate counter and a queue for each of the channels. Stimulation generator 58 may receive a control or timing signal from processor 50 to operate the rate counters. In some examples, stimulation generator 58 may utilize registers within memory 52 as the queues. Stimulation generator 58 may increment and decrement the queues as previously described. That is, stimulation generator 58 may increment a queue based on the corresponding rate counter and decrement the queue when stimulation is delivered on the corresponding channel. Stimulation generator 58 may also store and access other parameter values within memory 52 for managing the delivery of electrical stimulation and adjusting rate intervals. For example, stimulation generator 58 may store in memory 52 the minimum and maximum values for the recharge intervals.

As described above, stimulation generator 58 may adaptively deliver electrical stimulation on the two or more channels so as to maintain the programmed rates based on the queues and in accordance with the stimulation rules. Stimulation generator 58 may access stimulation rules stored within memory 52, e.g., as instructions executable by processor 50, and deliver stimulation therapy accordingly. Similarly, stimulation generator 58 may access recharge rules stored within memory 52, e.g., as instructions executable by processor 50, and adjust recharge intervals accordingly. One example configuration of stimulation generator 58 is described in greater detail below with respect to FIG. 5.

Additionally, example methods performed by stimulation generator 58 are described in greater detail below with respect to FIGS. 7-10.

Stimulation generator 58 may be electrically coupled to electrodes 48A-P via conductors of the respective lead, such as lead 12 in FIG. 1 or leads 32 in FIG. 2, in implementations in which electrodes 48A-P are carried by, or located on, leads. Stimulation generator 58 may be electrically coupled to one or more housing ("can") electrodes 48Q via an electrical conductor disposed within the housing of implantable stimulator 4 (FIG. 1) or implantable stimulator 34 (FIG. 3). A housing electrode 48Q may be configured to form a channel or an electrode configuration in conjunction with one or more of electrodes 48A-48P located on leads of the stimulator.

Each electrode 48A-Q may be coupled to a voltage or current source such that the pulse width, amplitude, and rate may be individually and selectively controlled. In an example in which stimulation generator 58 delivers electrical stimulation in the form of voltage pulses, each electrode 48A-Q may be coupled to a voltage supply/regulator through a stack of capacitors. Each of the capacitors in the stack may be charged with approximately the same amount of charge, the total sum of the charge across all of the capacitors being equal to a predetermined amount. To deliver the voltage pulse to the tissue, the capacitors may be simultaneously coupled to the electrode and discharge the stored charge to the tissue through the electrode.

In another example in which stimulation generator 58 delivers electrical stimulation in the form of voltage pulses, each electrode 48A-Q may use an inductor that builds charge on a capacitor to a predetermined value over multiple cycles. When the charge on the capacitor reaches the predetermined value, the pulse is delivered to the tissue by coupling the capacitor to the electrode.

Telemetry module 56 may include a radio frequency (RF) transceiver to permit bi-directional communication between implantable stimulator 4 and each of clinician programmer 20 and patient programmer 22. Telemetry module 56 may include an antenna 57. Antenna 57 may be formed, for example, by a conductive coil or wire embedded in a housing associated with implantable stimulator 4. Alternatively, antenna 57 may be mounted on a circuit board carrying other components of implantable stimulator 4 or take the form of a circuit trace on the circuit board. Telemetry module 56 may permit communication with clinician programmer 20 and patient programmer 22 in FIG. 1 or clinician programmer 40 and patient programmer 42 in FIG. 2, to receive, for example, new programs or program groups, or adjustments to programs or program groups.

Power source 54 may include a non-rechargeable primary cell battery or a rechargeable battery and may be coupled to power circuitry. However, the disclosure is not limited to examples in which the power source is a battery. In another example, a power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional examples, power source 54 may include a small rechargeable circuit and a power generation circuit to produce the operating power. Recharging may be accomplished through proximal inductive interaction between an external charger and an inductive charging coil within stimulator 4 or 34. In some examples, power requirements may be small enough to allow stimulator 4 or 34 to utilize patient motion at least in part and implement a kinetic energy-scavenging device to trickle charge a rechargeable battery.

Power source 54 may include a voltage converter, such as a DC-DC voltage converter, that converts the battery voltage to one or more voltages at different voltage levels. Stimulation generator 58 may use the different voltage levels to generate a supply voltage for delivering stimulation. For example, an array of capacitors and switches may be configured to convert the voltage from power source 54 into a supply voltage. As another example, stimulation generator 58 may use the voltage from power source 54 to charge a voltage supply capacitor module to provide a supply voltage at a desired level to one or more current regulators. In particular, current regulators within stimulation generator 58 may use the supply voltage to generate stimulation current pulses at desired current levels.

During delivery of a voltage or current pulse, as described above, the supply capacitor module may be partially discharged from an initial supply voltage level to a decreased supply voltage level. In some examples, stimulation generator 58 may recharge the supply capacitor module to the initial supply voltage level, e.g., between successive pulses, in accordance with the recharge intervals. In this manner, the supply voltage on the supply capacitor module at the beginning of each pulse may be recharged up to the initial supply voltage level. At the end of delivery of each pulse, the supply voltage on the supply capacitor module may drop to a decreased supply voltage level due to discharge of the supply capacitance. However, if the stimulation generator is unable to fully recharge before delivering the next stimulation pulse, the supply capacitor may not be fully recharged when the next stimulation pulse is delivered. This may result in amplitude sag, a charge-imbalance (e.g., from inadequate recharge), or both. In some examples, stimulation generator 58 automatically adjusts the recharge intervals to be as long as possible while maintaining the programmed pulse rates. In this way, stimulation generator 58 may also adjust the recharge intervals to extend the life of power source 54.

Figure 4:
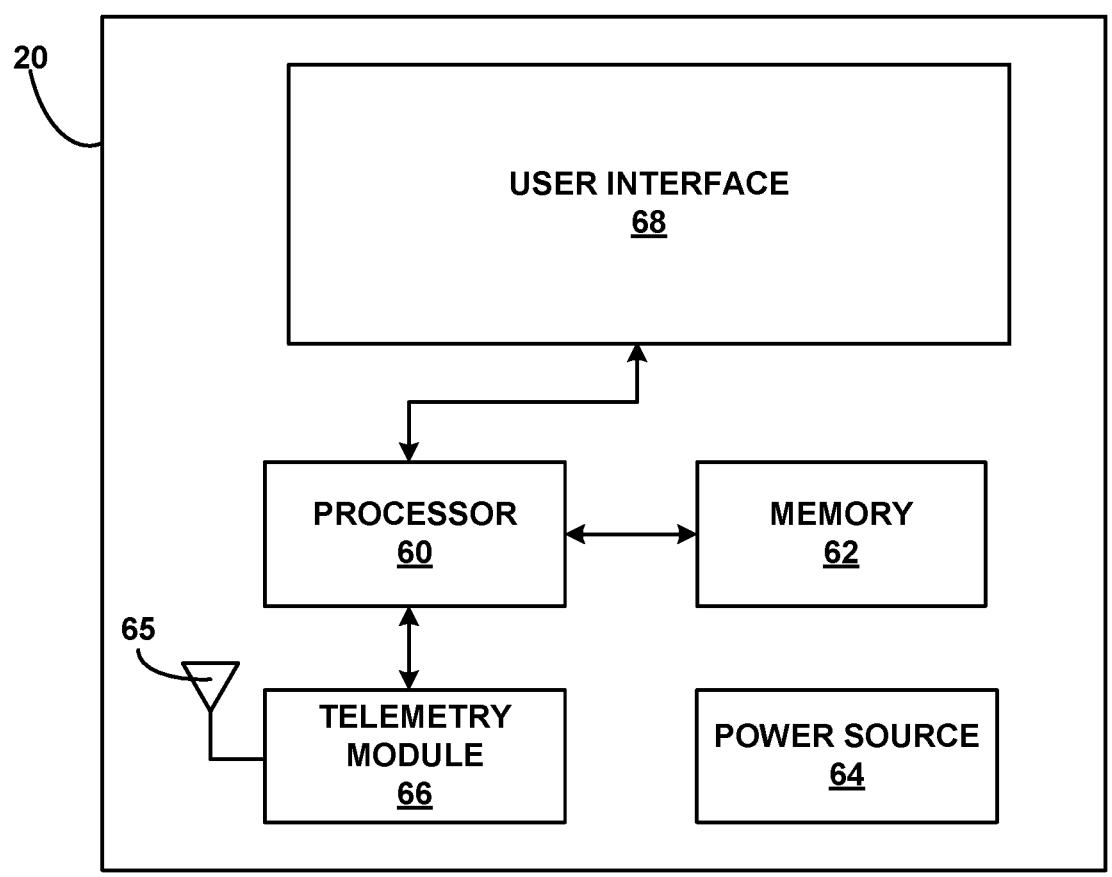
FIG. 4 is a block diagram illustrating various example components of an external programmer for use with the electrical stimulator.

FIG. 4 is a functional block diagram illustrating various components of an external programmer 20 for an implantable stimulator such as stimulator 4 (FIG. 1) or stimulator 34 (FIG. 2). Although the components shown in FIG. 4 are described with reference to external programmer 20 (FIG. 1), some or all of the components may also be included within clinician programmer 40 or patient programmer 42 as shown in FIG. 2, or patient programmer 22 as also shown in FIG. 1. As shown in FIG. 4, external programmer 20 includes processor 60, memory 62, telemetry module 66, user interface 68, and power source 64. In general, processor 60 controls user interface 68, stores and retrieves data to and from memory 62, and controls transmission of data with implantable stimulator 4 through telemetry module 66. Processor 60 may take the form of one or more microprocessors, controllers, DSPs, ASICS, FPGAs, or equivalent discrete or integrated logic circuitry. The functions attributed to processor 60 herein may be embodied as software, firmware, hardware or any combination thereof.

Memory 62 may store instructions that cause processor 60 to provide various aspects of the functionality ascribed to external programmer 20 herein. Memory 62 may include any fixed or removable magnetic, optical, or electrical media, such as RAM, ROM, CD-ROM, magnetic disks, EEPROM, or the like. Memory 62 may also include a removable memory portion that may be used to provide memory updates or increases in memory capacities. A removable memory may also allow patient data to be easily transferred to another computing device, or to be removed before programmer 20 is used to program therapy for another patient. Memory 62 may also store information that controls operation of implantable stimulator 4 or 34, such as electrical stimulation parameters.

A clinician or patient may interact with user interface 68 in order to, for example, manually select, change or modify programs, adjust voltage or current amplitude, provide efficacy feedback, or view stimulation data. User interface 68 may include a screen and one or more input buttons that allow external programmer 20 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Telemetry module 66 allows the transfer of data to and from stimulator 4 (or stimulator 34 in FIG. 2). Telemetry module 66 may communicate automatically with stimulator 4 at a scheduled time or when the telemetry module detects the proximity of the stimulator, for example. Alternatively, telemetry module 66 may communicate with stimulator 4 when signaled by a user through user interface 68. To support RF communication, telemetry module 66 may include appropriate electronic components, such as amplifiers, filters, mixers, encoders, decoders, and the like.

Programmer 20 may communicate wirelessly with implantable stimulator 4 using, for example, RF communication or proximal inductive interaction. This wireless communication is possible through the use of telemetry module 66, which may be coupled to an internal antenna or an external antenna. Telemetry module 66 may be similar to telemetry module 56 (FIG. 3) of implantable stimulator 4 (FIG. 1). Accordingly, telemetry module 66 may include antenna 67 which may be an internal or external antenna similar to antenna 57 previously described with respect to FIG. 3.

Programmer 20 may also be configured to communicate with another computing device via wireless communication techniques, or direct communication through a wired, e.g., network, connection. Examples of local wireless communication techniques that may be employed to facilitate communication between programmer 20 and another computing device include RF communication based on the 802.11 or Bluetooth specification sets, infrared communication, e.g., based on the IrDA standard.

Power source 64 delivers operating power to the components of programmer 20. Power source 64 may be a rechargeable battery, such as a lithium ion or a nickel metal hydride battery. Other rechargeable or conventional batteries may also be used. In some cases, external programmer 20 may be used when coupled to an alternating current (AC) outlet, e.g., AC line power, either directly or via an AC/DC adapter. Power source 64 may include circuitry to monitor power remaining within a battery. In this manner, user interface 68 may provide a current battery level indicator or low battery level indicator when the battery needs to be replaced or recharged. In some cases, power source 64 may be capable of estimating the remaining time of operation using the current battery.

Figure 5:
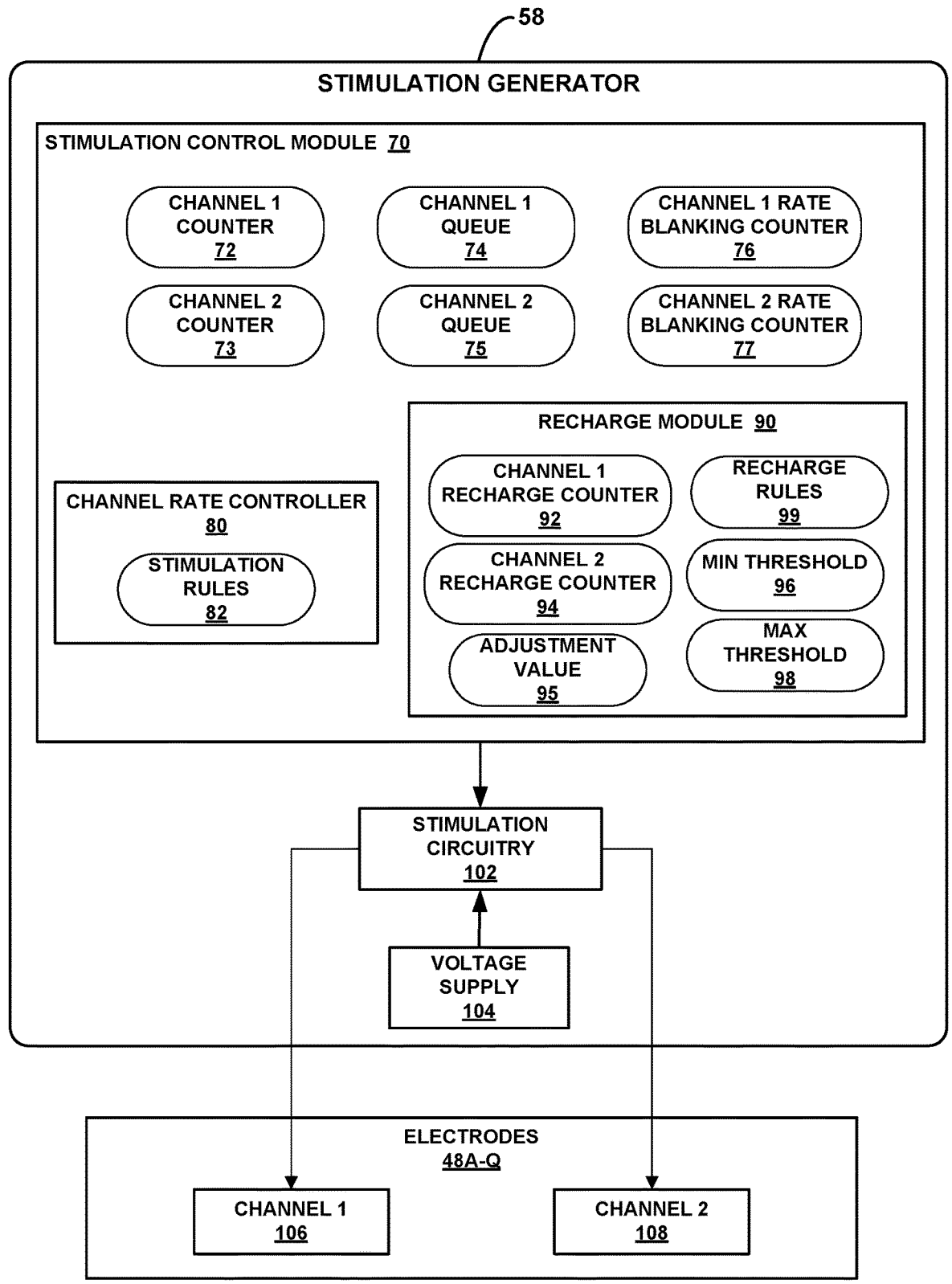
FIG. 5 is a block diagram illustrating various components of an example stimulation generator for use in the implantable electrical stimulator of FIG. 3.

FIG. 5 is a block diagram illustrating various components of an example stimulation generator 58 that may be used in accordance with the techniques of this disclosure. Stimulation generator 58 may be configured to provide the electrical stimulation therapy of an implantable stimulator, e.g., stimulator 4 and stimulator 34, as described with reference to FIGS. 1 and 2. Although described with respect to implantable stimulator 4, stimulation generator 58 may also be used for implantable stimulator 34, or other types of stimulators, such as external stimulators. In the example depicted in FIG. 5, stimulation generator 58 is configured to adaptively deliver electrical stimulation pulses to patient 6 so as to maintain the programmed rates for two or more channels and automatically adjust recharge signals associated with the electrical stimulation pulses. In some examples, stimulation generator 58 may adaptively deliver electrical stimulation pulses and automatically adjust recharge signals based on instructions executed by processor 50 (FIG. 3).

In the example shown in FIG. 5, stimulation generator 58 includes stimulation control module 70, stimulation circuitry 102, and voltage supply 104. Stimulation generator 58 is also illustrated as being coupled to electrodes 48A-Q. Generally, stimulation generator 58 is described with respect to FIG. 5 as delivering electrical stimulation to patient 6 via two channels, e.g. channel 1 106 and channel 2 108. Throughout this disclosure, channel 1 106 is described as being programmed to deliver electrical stimulation at a higher rate than channel 2 108. Hence, channel 1 106 is referred to as a "higher-rate channel" and channel 2 108 is referred to as a "lower-rate channel" throughout this disclosure. As previously described, channel 1 106 and channel 2 108 may be programmed to include any combination of electrodes 48A-Q.

Although stimulation generator 58 is shown in FIG. 5 as delivering electrical stimulation to patient 6 via two independent channels, it should be understood that stimulation generator 58 may be configured to deliver electrical stimulation to patient 6 via more than two channels. That is, stimulation generator 58 may be configured to deliver electrical stimulation to patient 6 via three channels, each of which may be programmed to deliver electrical stimulation at a different rate, and adaptively deliver of stimulation via the three channels so as to maintain the programmed rates.

Voltage supply 104 receives operating power from power source 54 (FIG. 3). In turn, voltage supply 104 may provide a supply voltage to stimulation circuitry 102. Voltage supply 104 may supply a high supply voltage and a low supply voltage, e.g., voltage levels used by stimulation circuitry 102 to generate stimulation pulses. In some examples, stimulation circuitry 102 may be configured for delivering stimulation to the patient in the form of voltage pulses. In other examples, stimulation circuitry 102 may be configured for delivering stimulation to the patient in the form of current pulses.

Stimulation circuitry 102 may include a charging circuit and a capacitor module. The charging circuit may selectively apply energy from voltage supply 104 to the capacitor module for generation and delivery of a supply voltage at a desired supply voltage level for generating stimulation pulses and corresponding recharge signals. Using capacitors and switches, for example, a capacitor module associated with voltage supply 104 may be configurable, e.g., based on signals from processor 50, to store a desired voltage level that provides a supply voltage level for delivery of stimulation pulses at a rate specified by a program. In an example in which the capacitor module includes a stimulation capacitor for each of the electrodes, e.g., a switched inductor configuration, the charging circuit may include switches that cycle on and off to build charge on the selected stimulation electrodes. In another example in which the capacitor module includes a capacitor stack, e.g., a stacked capacitor configuration, the capacitor may also include switches to selectively adjust the number of capacitors used in a capacitor stack to produce the stimulation pulse. In some examples, switches within the capacitor module also may control the widths of the pulses based on signals from processor 50.

Stimulation control module 70 controls stimulation circuitry 102 to adaptively deliver of electrical stimulation and adjust recharge intervals for the electrical stimulation as previously described in this disclosure. Stimulation control module 70 may include one more microprocessors, microcontrollers, digital signal processors (DSPs), application-specific integrated circuits (ASICs), field-programmable gate arrays (FPGAs), or other integrated or discrete logic circuitry. In operation, stimulation control module 70 may control delivery of electrical stimulation according to one or more programs that specify stimulation parameters such as electrode combinations (channels), electrode polarity, stimulation current or voltage pulse amplitude, pulse rate, and/or pulse width.

In the example of FIG. 5, stimulation control module 70 may include channel rate controller 80 and recharge module 90. Stimulation control module 70 may also include various parameters that are used by channel rate controller 80 and recharge module 90, including channel 1 rate counter 72, channel 2 rate counter 73, channel 1 queue 74, channel 2 queue 75, channel 1 rate blanking counter 76, and channel 2 rate blanking counter 77. Channel 1 counter 72 and channel 2 counter 73 operate independently of each other and are used for tracking the programmed rate of electrical stimulation delivered via channel 1 102 and channel 2 108, respectively. Although counters 72 and 73 may count upwards or downwards, for simplicity, this disclosure refers to example implementations in which the counters count downwards. Rate blanking counters 76, 77 are used to set rate blanking intervals for a corresponding channel and are used to space pulses on the same channel to avoid delivering consecutive pulses on the same channel at an unnecessarily high rate. Rate blanking intervals are shown and described in detail below with respect to FIG. 6.

Channel 1 queue 74 and channel 2 queue 75 are used for tracking the backlog of pulses for channel 1 106 and channel 2 108. Stimulation control module 70 may increment either channel 1 queue 72 or channel 2 queue 73 when the corresponding one of channel 1 counter 72 or channel 2 counter 73 reaches zero, indicating that it is time to pulse in accordance with the programmed rate. Stimulation control module 70 may decrement channel 1 queue 72 or channel 2 queue 73 when a stimulation pulse is delivered on a corresponding one of channel 1 106 and channel 2 108. Accordingly, channel 1 queue 74 and channel 2 queue 75 represent a backlog of pulses for channel 1 106 and channel 2 108, respectively.

Channel 1 rate blanking counter 76 and channel 2 rate blanking counter 77 determine the rate blanking intervals for the corresponding channel and are used to space pulses on the same channel to avoid delivering consecutive pulses on the same channel at an unnecessarily high rate. Generally, channel 1 rate blanking counter 76 and channel 2 rate blanking counter 77 may correspond to the programmed rate for channel 1 and channel 2, respectively. That is, channel 1 rate blanking counter 76 and channel 2 rate blanking counter 77 may count down from the same value as channel 1 rate counter 72 and channel 2 rate counter 73, respectively. However, as previously described, rate blanking counters 76 and 77 may be triggered when a stimulation pulse is delivered on a corresponding channel, whereas rate counters 72 and 73 are not synchronized with delivering pulses. Instead, rate counters 72 and 73 automatically reset when the counter expires. In this way, rate counters 72 and 73 can be used for tracking the backlog of pulses in queues 74 and 75, respectively.

In some examples, channel rate controller 80 may adjust rate blanking counters 76 and 77. For example, channel rate controller 80 may adjust one or both of rate blanking counters 76 and 77 to shorten the corresponding rate blanking interval when there is a backlog of pulses, i.e., when the stimulator needs to "catch up."

Generally, channel rate controller 80 adaptively delivers stimulation pulses so as to maintain the rates programmed for channels 1 and 2. With respect to FIG. 5, channel rate controller 80 controls stimulation circuitry 102 and, more particularly, the switches within stimulation circuitry 102 (not shown), to generate stimulation pulses on channel 1 106 and channel 2 108 in a way that maintains the programmed rates for the channels. Specifically, channel rate controller 80 may control stimulation circuitry 102 based on channel 1 counter 72, channel 1 queue 74, channel 2 counter 73, and channel 2 queue 75 and in accordance with stimulation rules 82. Stimulation rules 82 provide guidelines for handling the backlog of pulses.

Stimulation rules 82 may include pulse delaying the higher-rate channel while the lower-rate channel delivers pulses. As the higher-rate channel pulse delays over time, the backlog for the higher-rate rate channel increases. At the same time, the lower-rate channel backlog may also increase, but at a slower rate than the backlog for the higher-rate channel. When the backlog for the higher-rate channel exceeds the backlog for the lower-rate channel, consecutive pulses may be delivered on the higher-rate channel in order for the higher-rate channel to "catch up" to the programmed rate. As a result, the average rates for the higher-rate and lower-rate channels will be maintained. That is, the instantaneous rate over a few pulses on a channel may increase, such as when the higher-rate channel "catches up," but this occurs relatively infrequently. In some examples, the instantaneous rate over a few pulses on a channel may increase within a range of approximately 3% to approximately 6%. Consequently, the average rate for both the higher-rate and lower-rate channel is maintained.

In operation, channel rate controller 80 monitors channel 1 queue 74 and channel 2 queue 75 in accordance with stimulation rules 82. Channel rate controller 80 may monitor queues 74 and 75 substantially continuously. For example, channel rate controller 80 may monitor queues 74 and 75 for each clock cycle that counters 72 and 73 are incremented for a counter that counts upward (or decremented for a counter that counts downward). Specifically, channel rate controller 80 monitors queues 74 and 75 to determine when to deliver stimulation pulses on channel 1 106 and channel 2 108 in accordance with stimulation rules 82. As one example, channel rate controller 80 may deliver stimulation pulses using the following stimulation rules or conditions:

1) One of queues 74 and 75 is populated, i.e., has a value of one or more, indicating that a pulse is waiting to be delivered on one of channel 1 106 and channel 2 108;

2) There is not another stimulation pulse being delivered or recharge pulse occurring;

3) The channel that wants to pulse, which is determined by rule 4 provided below, has waited long enough since its last pulse. In other words, the rate blanking counter for the channel has expired; and 4) The stimulation pulse is delivered on the channel with the largest queue, i.e., the queue with the largest value. If the queues have the same value, then the stimulation pulse is delivered on the channel that is not rate blanking.

Figure 6:
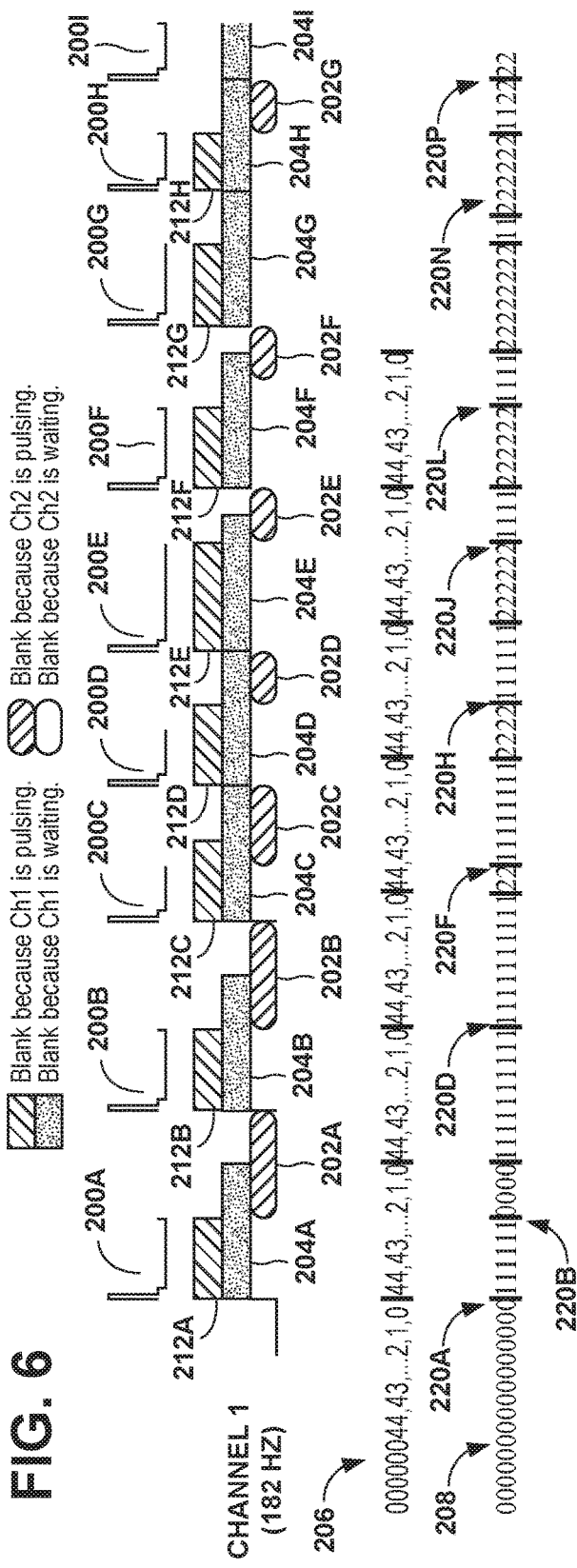
FIG. 6 illustrates an example timing diagram for delivering electrical stimulation over multiple channels with independent rates.
Figure 6:
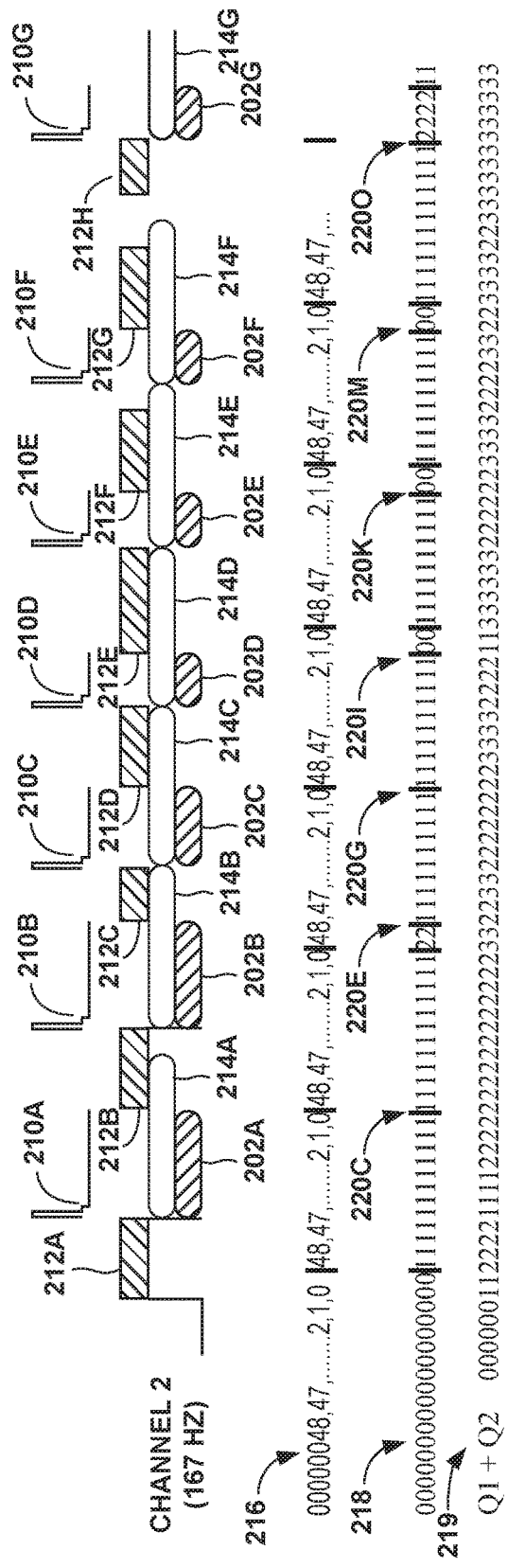

The first condition may indicate that one of channel rate counters 72 and 73 has expired so that one of queues 74 and 75 is populated and, therefore, a pulse should be delivered on the corresponding channel. The second condition may indicate that both channels be inactive so that stimulation circuit 102 is available for delivering a stimulation pulse. The third condition may indicate that the rate blanking interval has expired for the selected channel. The rate blanking interval is determined by rate blanking counters 76 and 77. Thus, channel rate controller 80 may examine the appropriate one of rate blanking counters 76 and 77 to determine if the third condition is satisfied. Thus, the first three conditions determine if a stimulation pulse should be delivered. The fourth condition determines the channel on which the stimulation pulse should be delivered. Channel rate controller 80 examines queues 74 and 75 to determine which channel to select. Accordingly, channel rate controller 80 may first determine the value of queues 74 and 75. When one of queues 74 and 75 is larger than the other, rate controller examines the rate blanking counter that corresponds to the largest queue. If the rate blanking counter has expired, rate controller 80 selects the channel with the largest queue for delivering stimulation. If, however, queues 74 and 75 have the same value, rate controller 80 may examine rate blanking counters 76 and 77 to determine which channel is available to deliver a pulse. In the event that rate blanking counters 76 and 77 are both expired, channel rate controller 80 may deliver the stimulation pulse on either of channel 1 106 and channel 2 108. A timing diagram that serves as a working example for managing the delivery of stimulation pulses in accordance with the techniques of this disclosure is depicted in FIG. 6.

In this way, channel rate controller 80 may deliver a stimulation pulse when all the above conditions are satisfied. In particular, when the conditions are satisfied, channel rate controller 80 may send a control signal to stimulation control module 70 which then sends appropriate signals to stimulation circuitry 102 causing the stimulation pulse to be delivered on the selected channel.

In some examples, channel rate controller 80 may also adjust rate blanking counters 76 and 77, e.g., adjust the interval associated with the rate blanking counters. In operation, channel rate controller 80 triggers rate blanking counters 76 and 77 to begin counting, either up or down, when a stimulation pulse is delivered on the corresponding channel. While a rate blanking counter is active, e.g., counting up or down, the corresponding channel is not available for delivering a stimulation pulse, and is therefore essentially "blanked." In this disclosure, a channel is referred to as "rate blanking" when the rate blanking counter for the channel has not expired. When the rate blanking counter expires, the corresponding channel may be available for delivering a stimulation pulse.

Channel rate controller 80 may, in some examples, adjust the rate blanking interval when a channel needs to "catch up." For example, channel rate controller 80 may decrease the rate blanking interval for the higher-rate channel when the higher-rate channel has to catch-up. Decreasing the rate blanking interval for the higher-rate channel allows the higher-rate channel to catch up more quickly. In some examples, channel rate controller 80 may adjust the rate blanking interval based on the value of the corresponding queue. As an example, channel rate controller 80 may adjust the rate blanking interval proportional to the length of the corresponding queue within programmable limits.

Recharge module 90 adjusts the recharge signals associated with stimulation pulses delivered over channel 1 106 and channel 2 108 in a way that provides a trade-off between fidelity to the programmed stimulation rate and charge balance or amplitude sag. In some examples, recharge module 90 may adjust the recharge interval to be as long possible while maintaining fidelity to the programmed rate. In other examples, recharge module 90 may additionally or alternatively adjust the recharge amplitude. As an example, recharge module 90 may increase the recharge amplitude as the time interval for the recharge pulse is decreased in order to avoid amplitude sag or charge imbalance. In such examples, stimulator 4 may provide operate at a lower energy efficiency. Additionally, recharge module 90 may adjust recharge intervals without regard to the method used for delivering stimulation. Thus, recharge module 90 may operate as described in the following paragraphs in an example configuration in which a stimulator does not utilize channel rate controller 80. In the example of FIG. 5, however, recharge module 90 and channel rate controller 80 are each utilized.

In FIG. 5, recharge module 90 includes various parameters including channel 1 recharge counter 92, channel 2 recharge counter 94, adjustment value 95, minimum time value 96, maximum time value 98, and recharge rules 99. Recharge counters 92 and 94 may count either up or down and are used for tracking the recharge intervals for channel 1 106 and channel 2 108, respectively. Adjustment value 95 represents the time value by which the recharge interval may be adjusted. That is, the time value by which recharge counters 92 and 94 may be adjusted. In some examples, adjustment value 95 may store an adjustment value for each of the channels. An example value may be approximately 1.95 ms. In some examples, adjustment value 95 may be a fixed and predetermined value. In other examples, adjustment value 95 may be varied, for example, based on queues 74 and 75.

Minimum time value 96 may store the minimum interval time value that may used for channel 1 106 and channel 2108. Maximum time value 98 may store the maximum time value that may be used for recharging channel 1 106 and channel 2 108. In some examples, minimum time 96 may store a value of approximately 1.95 ms and maximum time 98 may store a value of approximately 7.8 ms. In other examples, recharge module 90 may be configured to store a minimum and time threshold value for each of the channels. This may be advantageous in examples in which stimulation pulses of different energy levels are delivered on each of the channels. For example, the high-energy channel may have a larger minimum time value than the low-energy value.

Recharge rules 99 provide guidelines for adjusting recharge counters 92 and 94. Again, amplitude sag may occur when stimulator circuitry 102 is not able to fully recharge before delivering the next stimulation pulse. Recharge module 90 adjusts recharge counters 92 and 94 so that amplitude sag is minimized or charge-balance is maintained while maintaining programmed pulse rates. Moreover, when amplitude sag or rate-limited charge-balance is not a factor, recharge module 90 may extend recharge counters 92 and 94 as much as possible while maintaining the programmed pulse rates. In this way, recharge module 90 may deplete power source 54 (FIG. 3) less rapidly, thereby extending the life of stimulator 4. In particular, recharge rules 99 provide rules for increasing and decreasing recharge counters 92 and 94 based on queues 74 and 75. In the example shown in FIG. 5, recharge module 90 increases and decreases recharge counters 92 and 94 by adjustment value 95 within the limits set by minimum value 96 and maximum value 98.

Similar to channel rate controller 80, recharge module 90 may monitor queues 74 and 75 substantially continuously. Alternatively, in an example like that shown in FIG. 5 in which stimulation control module 70 includes both channel rate controller 80 and recharge module 90, channel rate controller 80 may send a control signal to recharge module 90 that triggers recharge module 90 to examine queues 74 and 75. In such an example, channel rate controller 80 may send the control signal when a pulse is delivered on either one of channel 1 106 and channel 2 108. After receiving the control signal, recharge module 90 may determine whether to increase recharge counters 92 and 94, decrease recharge counters 92 and 94, or maintain the present recharge interval in accordance with recharge rules 99. For example, recharge module 90 may update recharge counters 92 and 94 after a recharge signal has been delivered on the corresponding channel. Consequently, recharge counters 92 and 94 may be set to an appropriate value when the next recharge signal is delivered.

As one example, recharge module 90 may adjust recharge counters 92 and 94 in accordance with the following rules:

1) If channel 1 queue value+channel 2 queue value=1, extend recharge interval within limits.

2) If channel 1 queue value+channel 2 queue value=2, maintain recharge intervals.

3) If channel 1 queue value+channel 2 queue value>2, reduce recharge interval within limits.

4) If both channels are rate-limit waiting, extend the recharge interval. In some examples, the recharge signal may be applied without regard to the set interval, i.e., without regard to the recharge counters. In such an example, the recharge signal may be allowed to extend to the maximum time threshold. Moreover, recharge module 90 may not, in some examples, update the corresponding recharge counter when the channels are rate limit waiting.

Each of the example rules provided above can be thought of as a use case. The use case is defined by queues 74 and 75 and, more particularly, the sum of the values in queues 74 and 75. The example rules may define the action or inaction to be taken for a given use case. A first use case may occur when the sum of the values in queues 74 and 75 is "1." When the first use case occurs, recharge module 90 may increase the recharge counter for the active channel, e.g., the channel on which the stimulation pulse is delivered. In some examples, in order to increase the efficiency of the stimulator, recharge module 90 may reduce the amplitude of the recharge signal, i.e., amplitude of the recharge signal, when increasing the recharge interval.

A second use case may occur when the sum of the values in queues 74 and 75 is "2." In this case, recharge module 90 does not adjust the recharge counter of the active channel because stimulator 4 is essentially "keeping up" with the programmed rates since neither of the channels has a backlog larger than "1."

A third use case occurs when the sum of the values in queues 74 and 75 is greater than "2." In this case, recharge module 90 decreases the recharge counter for the active channel by adjustment value 95 within the limits of minimum time value 96 and maximum time value 98. Recharge module 90 may decrease the recharge counter in this case because stimulator 4 is "falling behind" the programmed rates in delivering pulses. Decreasing the recharge counter in this case may allow stimulator 4 to more effectively maintain the programmed rate. However, as previously described, decreasing the recharge counter may result in amplitude sag or charge imbalance. In some examples, recharge module 90 may increase the amplitude of the recharge signal when decreasing the recharge counter in order to compensate for amplitude sag or charge imbalance.

A fourth use case occurs when channel 1 106 and channel 2 108 are rate-limit waiting. The channels are rate-limit waiting when recharge counters 92 and 94 have not yet expired. When this occurs, recharge module 90 may allow the recharge signal to continue to be applied to the channel past the time specified by channel 1 recharge counter 92 or channel 2 recharge counter 94. Recharge module 90 may allow the recharge signal to continue to be applied to the appropriate channel in order to take advantage of the idle time that occurs during rate-limit waiting. If recharge module 90 did not allow the recharge signal to be applied past the value stored in recharge counters 92, 94 stimulator 4 may not operate as efficiently.

Although FIG. 5 illustrates channel 1 counter 72, channel 2 counter 73, channel 1 queue 74, channel 2 queue 75, channel 1 rate blanking counter 76, channel 2 rate blanking counter 77, stimulation rules 82, channel 1 recharge counter 92, channel 2 recharge counter 94, adjustment value 95, minimum time value 96, maximum time value 98, and recharge rules 99 within stimulation generator 58, these parameters may be stored in memory 52 of stimulation generator 58. In particular, the parameters may be stored in registers of memory 52 which may be accessed by stimulation control module 70, channel rate controller 80, and recharge module 90. As such, FIG. 5 depicts one example configuration by which stimulation generator 58 and its modules may access and use the parameters.

It should be recognized that other configurations of recharge module 90 are possible. For example, recharge module 90 may be configured to adjust recharge intervals by selecting a recharge interval from a range of predetermined values. For example, recharge module 90 may be configured to adjust recharge intervals by selecting a recharge interval from one of 7.8 ms, 5.9 ms, 4.9 ms, 3.9 ms, 2.9 ms, 1.9 ms, 1.5 ms, and 0.976 ms. In such an example, recharge module 90 may increase the recharge interval by selecting the next largest interval value and decrease the recharge interval by selecting the next lowest interval value. Other ranges of interval values are contemplated.

FIG. 6 illustrates an example timing diagram for electrical stimulation therapy delivered according to the techniques described in this disclosure. FIG. 6 provides a working example for managing delivery of electrical stimulation by stimulation generator 58 over two independent channels in a way that maintains the programmed rates, and for adjusting recharge signals to provide a tradeoff between fidelity to programmed rate and amplitude sag or charge balance.

In FIG. 6, the timing diagram includes stimulation pulses 200A-I (collectively referred to as "stimulation pulses 200") delivered via channel 1 at a rate of approximately 182 Hz, and stimulation pulses 210A-G (collectively referred to as "stimulation pulses 210") delivered via channel 2 at a rate of approximately 167 Hz. Each of stimulation pulses 200 and 210 represent a stimulation pulse and a corresponding subsequent recharge pulse.

FIG. 6 also depicts the running value of channel 1 rate counter 206 and corresponding channel 1 queue 208, and the channel 2 rate counter 216 and corresponding channel 2 queue 218 (for each cycle over a period of time). Additionally, FIG. 6 depicts rate blanking intervals provided by rate blanking counter 76 for channel 1 at 204A-I and rate blanking intervals provided by rate blanking counter 77 for channel 2 at 214A-G. The value for the rate counters and queues are indicated for each cycle. In the example illustrated in FIG. 6, channel rate counters 206 and 216 are updated approximately every 30 microseconds. However, the timing diagram illustrated in FIG. 6 is not cycle-accurate because not every cycle is shown in the figure. Instead, the illustrated timing diagram is condensed in order to provide an example that more clearly shows the operation of the techniques described in this disclosure. Specifically, the timing diagram is condensed in a way that does not show redundant clock cycles in which parameters, such as queues and counters, do not change.

FIG. 6 also includes channel 1 blanking intervals 202A-G (collectively referred to as "blanking interval 202") and channel 2 blanking intervals 212A-H (collectively referred to as "blanking interval 212"). Blanking intervals 202 represent the time that channel 2 is pulsing or recharging. Accordingly, channel 1 cannot deliver a stimulation signal, such as a pulse, or recharge signal during blanking intervals 202 because stimulator 4 uses a single stimulation circuit for delivering stimulation and pulsing signals to both channels 1 and 2. Blanking intervals 212 represent the time that channel 1 is delivering a stimulation or recharging signal. Similarly, channel 2 cannot deliver a stimulation or recharge signal during blanking intervals 212.

FIG. 6 further includes channel 1 rate blanking intervals 204A-H (collectively referred to as "rate blanking intervals 204") and channel 2 rate blanking intervals 214A-H (collectively referred to as "rate blanking intervals 214"). Rate blanking counters 204 represent the time that channel 1 is rate blanking. That is, rate blanking intervals 204 correspond to channel 1 rate blanking counter 76 (FIG. 5). Similarly, rate blanking intervals 214 correspond to channel 2 rate blanking counter 77 (FIG. 5).

Additionally, FIG. 6 provides a representation of channel 1 queue 208 and channel 2 queue 218. Throughout this disclosure, channel 1 queue 208 is referred to as "$Q_1$ 208" and channel 2 queue 218 is referred to as "$Q_2$ 218" for conciseness. FIG. 6 further depicts a representation of the sum of $Q_1$ 208 and $Q_2$ 218, shown at 219 as Q1+Q2, and referred to as $Q_T$ 219 throughout this disclosure.

Generally, a stimulation pulse is delivered via one or more electrodes and then a recharge signal is delivered via the one or more electrodes in order to recover the charge delivered via the stimulation pulse, e.g., a current or voltage is applied in the reverse direction so that substantially zero net charge passes through the one or more electrodes. While charge is delivered and recovered on one of the channels, e.g., channel 1, the other channel, e.g., channel 2, is blanked by establishing a high impedance state across the corresponding electrodes. Blanking the inactive channel in this way prevents current from flowing through inactive electrodes while the active electrodes deliver stimulation or are being recharged.

The timing diagram of FIG. 6 may be divided into upper and lower portions. The upper portion of FIG. 6 illustrates the portion of the timing diagram that represents activity with respect to channel 1. The upper portion includes stimulation pulses 200 that depict electrical stimulation pulses delivered via channel 1, blanking intervals 212 for channel 2, and rate blanking intervals 204 for channel 1. Similarly, the lower portion of FIG. 6 illustrates activity with respect to channel 2. The lower portion of FIG. 6 includes stimulation pulses 210, blanking intervals 202, and rate blanking intervals 214.

FIG. 6 illustrates delivery of sixteen stimulation pulses, e.g., stimulation pulses 200 and 210, over channels 1 and 2. In the following paragraphs, the logic used to adaptively deliver the stimulation pulses and modify the recharge intervals is described in detail for each of the pulses in order to provide a comprehensive understanding of the described techniques. Reference numerals 220A-0 indicate the "pulse trigger" points of the timing diagram shown in FIG. 6. A pulse trigger occurs when the conditions for delivering a pulse are satisfied, e.g., when the stimulation rules are satisfied.

The timing diagram shown in FIG. 6 begins when channel 1 rate counter 206 and channel 2 rate counter 216 are activated. Channel 1 rate counter 206 and channel 2 rate counter 208 are activated at the same time and, if down-counters, count down from an initial value, e.g., an integer value, that corresponds to the programmed rate, to zero. For example, in FIG. 6, channel 1 rate counter 206 counts down from 44 (which corresponds to the programmed rate of 182 Hz) to zero and channel 2 rate counter 216 counts down from 48 (which corresponds to the programmed rate of 167 Hz) to zero. Rate counters 206 and 216 automatically reset themselves and begin counting down from the initial value when they expire. Additionally, when rate counters 206, 216 reach zero, the value in the corresponding one of queues 208, 218 is incremented. $Q_1$ 208 and $Q_2$ 218 may be populated according to a set of rules. For example, according the rules, a value of the population of a queue of a channel may be incremented when a rate counter associated with the channel reaches zero, and decremented when a stimulation and recharge pulse has been delivered.

The first pulse trigger 220A occurs in FIG. 6 when channel 1 rate counter 206 reaches zero, or expires, resulting in $Q_1$ 208 being incremented. So, immediately following pulse trigger 220A, the population of $Q_1$ 208 is "1" and the population of $Q_2$ 218 is "0." According to the rules provided in the description of FIG. 5, the first rule is satisfied because $Q_1$ 208 is populated. The second rule is satisfied because neither channel 1 nor channel 2 is active since stimulation has just been initiated. The third rule is satisfied because channel 1 has not previously delivered a pulse so it does not have to wait for a channel blanking period. Finally, the fourth rule indicates that the pulse may be delivered on channel 1 because $Q_1$ 208 ("1") is larger than $Q_2$ 218 ("0").

As a result, stimulation generator 58 delivers stimulation pulse 200A and its associated recharge signal on channel 1. Delivering stimulation pulse 200A triggers rate blanking for channel 1 which is represented by channel 1 rate blanking interval 204A, and blanking of channel 2 which is represented by channel 2 blanking interval 212A. Stimulation generator 58 blanks channel 2, e.g., by establishing a high impedance state across the corresponding electrodes, for the duration of stimulation pulse 200A. The duration of channel 1 stimulation pulses 200, e.g., stimulation pulse 200A, and channel 2 stimulation waveforms 210 are controlled by the programmed stimulation parameters, such as pulse amplitude and width, and recharge interval for the corresponding channel. As previously described, the recharge interval for channel 1 may be set to an initial value, e.g., approximately 3.9 ms, and is controlled by recharge counter 92. In some examples, recharge counter 92 is updated at the end of every recharge signal delivered on channel 1. So, in FIG. 6, the recharge interval for pulse 210A, i.e., recharge counter 92, is updated at 220B. In other examples, however, the recharge interval may be updated at the beginning of a pulse.

While stimulation generator 58 delivers stimulation waveform 200A to the patient via channel 1, channel 2 rate counter 216 expires and a rate trigger occurs. In this disclosure, a rate trigger occurs when one of the rate counters reaches zero. Thus, a rate trigger occurs when channel 2 rate counter 216 reaches zero. When this occurs, rate counter 216 resets itself and also triggers, or causes, channel 2 queue 218 to increment. Other parameters may also be updated as necessary, such as incrementing $Q_T$ 219. In FIG. 6, channel 2 rate counter 216 causes a rate trigger some time after delivery of stimulation waveform 200A begins. With reference to FIG. 6, the programmed rate of channel 2 corresponds to a value of 48 and the programmed rate of channel 1 corresponds to a value of 44, a difference of 4, so rate counter 216 causes a rate trigger four "clock cycles" after delivery of stimulation waveform 200A begins. At the rate trigger, stimulation generator 58 increments $Q_2$ 218 and updates $Q_T$ 219.

A number of cycles after this rate trigger, stimulation and recharge pulse 200A terminates and pulse trigger 220B occurs. At pulse trigger 220B, stimulation generator 58 decrements $Q_1$ 208 because stimulation and recharge pulse 200A has been delivered. As a result, the population of $Q_1$ 208 is "0," the population of $Q_2$ 218 is "1", and thus the population of $Q_T$ 219 is "1." According to the stimulation rules, the first rule is satisfied because $Q_2$ 218 is populated. The second rule is satisfied because channel 1 is no longer active after stimulation and recharge pulse 200A has been delivered. The third rule is satisfied because stimulation has not yet been delivered via channel 2. Finally, the fourth rule indicates that stimulation may be delivered on channel 2 because channel 1 is rate blanking. That is, because $Q_2$ 218 and $Q_1$ 208 have a population of "1" at the clock cycle prior to pulse trigger 200B, the fourth rule indicates that stimulation may be delivered on channel 2 because the rate blanking interval for channel 1, i.e., rate blanking interval 204A, has not expired.

Accordingly, stimulation generator 58 delivers stimulation and recharge pulse 210A via channel 2 and triggers rate blanking interval 214A at pulse trigger 220B. Stimulation generator 58 also blanks channel 1, e.g., by establishing a high impedance state across the corresponding electrodes, for the duration of stimulation and recharge pulse 210A, which is represented by blanking timing 202A. The duration of stimulation and recharge pulse 210A and, correspondingly, blanking timing 202A, is controlled by the programmed stimulation parameters, such as pulse amplitude and width, and recharge interval for channel 2. Similar to the recharge interval for stimulation and recharge pulse 200A, the recharge interval for stimulation and recharge pulse 210A may be determined by a default value, e.g., 3.9 ms. In the example illustrated in FIG. 6, channels 1 and 2 each have an independently controlled recharge interval. As will be described in the following paragraphs, the recharge intervals for channels 1 and 2 are adjusted based on the corresponding previous recharge interval. Also, the recharge interval is updated at the end of every recharge based on the state of the queue of the prior cycle. Thus, the recharge interval for channel 2 for waveform 210A is determined by $Q_T$ 219 at the cycle prior to pulse trigger 220B. The population of $Q_T$ 219 at the cycle prior to rate trigger 220B is "2." Accordingly, the recharge interval for channel 2 at pulse trigger 220B does not change from the default value, in accordance with the recharge interval rules.

While stimulation generator 58 delivers stimulation waveform 210A over channel 2, channel 1 rate counter 206 reaches zero and causes a rate trigger. In FIG. 6, the rate trigger occurs some time following pulse trigger 220B. Accordingly, stimulation generator 58 increments $Q_1$ 208 from "0" to "1" and updates $Q_T$ 219 from "1" to "2."

The next pulse trigger, i.e., pulse trigger 220C, occurs when stimulation generator 58 completes delivery of stimulation waveform 210A. At pulse trigger 220C, stimulation generator 58 decrements $Q_2$ 218 because stimulation and recharge pulse 210A was just delivered, but immediately increments $Q_2$ 218 because channel 2 pulse rate counter 216 reaches zero and causes a rate trigger. As a result, the population of both $Q_1$ 208 and $Q_2$ 218 is "1." The first stimulation rule is satisfied because both $Q_1$ 208 and $Q_2$ 218 are populated. The second stimulation rule is satisfied because channel 2 is no longer delivering stimulation and channel 1 has been blanked while stimulation was delivered over channel 2. The third stimulation rule is satisfied because blanking timing 204A has terminated. The fourth stimulation rule indicates that stimulation may be delivered via channel 1 because both queues have the same value, and if both queues have the same value, then the channel that is not being "blanked," e.g., rate blanked, is selected.

Consequently, stimulation generator 58 delivers stimulation and recharge pulse 200B on channel 1. Stimulation generator 58 also triggers rate blanking interval 204B and blanking of channel 2 represented by blanking timing 212B. In the example of FIG. 6, the duration of recharge interval for channel 1 is determined at the end of the previously delivered pulse, i.e., stimulation and recharge pulse 210A. Because the population of $Q_T$ 219 is "2" at the clock cycle prior to pulse trigger 220C, the recharge interval for channel 1 remains the same, according to the recharge interval rules. Accordingly, the recharge interval for channel 1 remains the same as that for stimulation pulse 200A, e.g., approximately 3.9 ms. As a result, stimulation and recharge pulse 200B and blanking timing 212B have a duration of the pulse width of the stimulation pulse plus approximately 3.9 ms.

The next pulse trigger, pulse trigger 220D, occurs when stimulation and recharge pulse 200B has been delivered. Because stimulation and recharge pulse 200B has been delivered, $Q_1$ 208 is decremented. However, channel 1 rate counter 206 also causes a rate trigger at pulse trigger 220D at coincidentally close to the same time, so $Q_1$ 208 is also incremented, resulting in a value of "1." Thus, the population of both $Q_1$ 208 and $Q_2$ 218 is "1." Thus, the first, second, third, and fourth stimulation rules all apply in the same manner as previously described with respect to pulse triggers 220B and 220C. Consequently, stimulation is delivered via channel 2 because channel 1 is rate blanking, i.e., because rate blanking interval 204B has not expired.

Accordingly, stimulation generator 58 delivers stimulation waveform 210B via channel 2 as shown in FIG. 6. In particular, stimulation generator 58 delivers stimulation waveform 210B without changing the associated recharging time for channel 2 because the population of $Q_T$ 219 at pulse trigger 220D is "2." Stimulation generator 58 also provides rate blanking in the form of rate blanking interval 214B and blanks channel 1 as shown by blanking waveform 202B.

Prior to the next pulse trigger, i.e., pulse trigger 220E, channel 2 rate counter 216 expires causing a rate trigger and thereby also incrementing $Q_2$ 218 from "1" to "2." However, at pulse trigger 220E, pulse 210B has been delivered, so $Q_2$ 218 is decremented. Thus, the population of both $Q_2$ 218 and $Q_1$ 208 at pulse trigger 220E is, again, "1." Consequently, the first, second, third, and fourth stimulation rules again apply in the same manner as previously described with respect to pulse trigger 220C. Accordingly, stimulation generator 58 delivers stimulation waveform 200C via channel 1.

However, because $Q_T$ 219 is "3" at the clock cycle prior to pulse trigger 220E, the recharge interval for channel 1 shortens and waveform 200C and blanking timing 212C have lesser duration than waveform 200B and blanking timing 212B. For example, if the initial recharge interval for channel 1 was 3.9 ms, the recharge interval may decrease by 1.95 ms (or other amount). In such an example, the recharge interval for waveform 200C may be 1.95 ms. In FIG. 6, stimulation generator 58 also provides rate blanking associated with waveform 200C in the form of rate blanking interval 204C.

While stimulation and recharge pulse 200C is delivered, channel 1 counter 206 expires causing a rate trigger which also increments $Q_1$ 208. As a result, $Q_1$ 208 has a value of "2" until stimulation pulse 200C terminates at pulse trigger 220F. At pulse trigger 220F, $Q_1$ 208 is decremented and, thus, has a value of "1" and $Q_2$ 218 again also has a value of "1." Consequently, the stimulation rules are satisfied in a similar manner as described previously with respect to pulse triggers 220B and 220D and stimulation generator 58 delivers stimulation pulse 210C on channel 2. In particular, stimulation pulse 210C and blanking pulse 202C are associated with a decreased recharge interval because $Q_T$ 219 is "3" at the clock cycle prior to pulse trigger 220F. In FIG. 6, however, waveform 210C is not shown as having an interval that is shortened by the same amount as waveform 200C because both channels 1 and 2 are rate limit waiting. That is, because rate blanking interval 204C has not yet expired (and thus channel 1 is not available for delivering stimulation), the recharge interval for waveform 210C is allowed to extend past the otherwise "shortened" recharge interval. Specifically, the recharge interval for waveform 210C is allowed to extend to the expiration of rate blanking interval 204C At pulse trigger 220F, stimulation generator 58 also provides rate blanking in the form of rate blanking interval 214C.

Blanking interval 204C expires, causing cessation of stimulation pulse 210C and causing the next pulse trigger 220G. Near pulse trigger 220G, channel 2 rate counter 208 expires and causes a rate trigger. Thus, $Q_2$ 218 is incremented, but $Q_2$ 218 is also decremented because of the termination of stimulation pulse 210C. As a result, both $Q_1$ 208 and $Q_2$ 218 have a value of "1" and $Q_T$ 219 has a value of "2." Again, the stimulation rules are satisfied in a similar manner as previously described with respect to pulse trigger 220E. Accordingly, stimulation generator 58 delivers stimulation waveform 200D on channel 1 and blanks channel 2 as shown by blanking timing 214D. Because $Q_T$ 219 has a value of "2" at pulse trigger 220G, the recharge interval for both stimulation pulse 200D and blanking timing 214D is unchanged. As previously described, the recharge interval for the previously delivered stimulation and recharge waveform 200C delivered was shortened. In FIG. 6, stimulation and recharge waveform 200D is not illustrated as having the same shortened recharge interval as waveform 200C because channels 1 and 2 are rate limit waiting. Specifically, channel 2 is rate limit waiting because rate blanking interval 214C has not yet expired thereby preventing stimulation from being delivered on channel 2. Instead, waveform 200D is allowed to extend past the shortened recharge interval until rate blanking interval 214C expires. In FIG. 6, stimulator 58 also triggers rate blanking interval 204D at pulse trigger 220G.

Pulse trigger 220H and termination of pulse waveform 200D are caused by the expiration of blanking interval 214C. At pulse trigger 220H, $Q_1$ 208 again has a value of "1" because $Q_1$ 208 is incremented due to a rate trigger caused by channel 1 rate counter 206 and decremented due to the termination of stimulation waveform 200D. $Q_2$ 218 also has a value of "1" at pulse trigger 220H. Thus, stimulation generator 58 delivers stimulation waveform 210D on channel 2 in accordance with the stimulation rules. The recharge interval associated with stimulation waveform 210D and corresponding blanking waveform 202D decreases because $Q_T$ 219 has a value of "3" at the end of waveform 210D, i.e., $Q_T$ 219 is "3" at the clock cycle prior to trigger 220H. There is no rate limit waiting associated with waveform 210D because rate blanking interval 204D expires within the shortened recharge interval for channel 2. Rate blanking interval 214D is also triggered at pulse trigger 220H.

The next pulse trigger, i.e., pulse trigger 220I, is triggered by the expiration of waveform 210D. At pulse trigger 220I, $Q_2$ 218 is decremented causing the value of $Q_1$ 208 to be "1" and the value of $Q_2$ 218 to be "0." Based on the stimulation rules, stimulation generator 58 delivers stimulation and recharge waveform 200E on channel 1 and blanks channel 2 as shown by blanking timing 212E. Stimulation generator 58 also allows the recharge interval for waveform 200E to remain unchanged because $Q_T$ 219 is "2" at the clock cycle prior to pulse trigger 220I. In FIG. 6, however, stimulation generator 58 allows the recharge interval to extend because channels 1 and 2 are rate limit waiting. In particular, waveform 200E is allowed to extend to the expiration of rate blanking interval 214D. Rate blanking interval 204E also begins at pulse trigger 220I.

While stimulation pulse 200E is delivered, both channel 1 rate counter 206 and channel 2 rate counter 216 cause rate triggers. As a result, both $Q_1$ 208 and $Q_2$ 218 are incremented. However, sometime near the termination of stimulation pulse 200E, which happens to coincide with the next pulse trigger 220J in FIG. 6, $Q_1$ is decremented. Thus, both $Q_1$ 208 and $Q_1$ 218 have a value of "1" at pulse trigger 220J. Consequently, according to the stimulation rules, stimulation generator 58 delivers stimulation, in the form of stimulation and recharge waveform 210E, on channel 2 because channel 1 is rate blanking. Additionally, the recharge interval for waveform 210E is shortened, within the predetermined limits, because $Q_T$ 219 is "3" for the clock cycle prior to pulse trigger 220J. In FIG. 6, the duration of waveform 210E is shown to be approximately the same as the duration of waveform 210D because the recharge interval was already decreased to the minimum value for waveform 210D. Accordingly, the recharge interval for waveform 210E cannot be decreased any further. In FIG. 6, stimulation generator 58 also blanks channel 1 while delivering stimulation pulse 210E as shown by blanking timing 202E. Additionally, rate blanking interval 214E begins at pulse trigger 220J.

The next pulse trigger, i.e., pulse trigger 220K, is triggered by the termination of stimulation and recharge waveform 210E. Channel 1 rate counter 206 also causes a rate trigger sometime near pulse trigger 220K. Accordingly, $Q_1$ 208 is incremented and $Q_2$ 218 is decremented so that the values of $Q_1$ 208 and $Q_1$ 218 are "2" and "0" at pulse trigger 220K. Consequently, stimulation generator 58 delivers stimulation and recharge waveform 200F on channel 1 while blanking channel 2, as shown by blanking timing 212F. Rate blanking interval 204F also begins at pulse trigger 220K. Because the sum of the values in $Q_1$ 208 and $Q_1$ 218 is "2," i.e., $Q_T$ 219 is "2," the recharge interval for waveform 200F is not adjusted. As previously described, the recharge interval for channel 1 may already be set to a minimal value in FIG. 6. In FIG. 6, however, waveform 200F is allowed to extend past the predetermined recharge interval because channels 1 and 2 are rate limit blanking.

During stimulation pulse 200F, channel 2 rate counter 216 expires causing a rate trigger, and thereby incrementing $Q_2$ 218 to a value of "1." Additionally, $Q_1$ 208 is decremented at the termination of stimulation waveform 200F to a value of "1." Further, rate blanking interval 214E has not yet terminated when stimulation pulse 200F has been delivered. Rate blanking interval 204F also has not yet terminated. Thus, a stimulation pulse cannot be delivered immediately following stimulation pulse 200F. As a result, stimulation generator 58 delays until stimulation can be delivered on one of the channels in accordance with the stimulation rules.

Accordingly, stimulation generator 58 delivers stimulation pulse 210F on channel 2 at pulse trigger 220L, which occurs at the termination of rate blanking interval 214E, in accordance with the stimulation rules. In particular, stimulation generator 58 delivers stimulation pulse 210F on channel 2 because both $Q_2$ 218 and $Q_1$ 208 have a value of "1" and channel 1 is rate blanking. The recharge interval for stimulation pulse 210F is not adjusted since $Q_T$ 219 has a value of "2" and, thus, may remain at a minimal threshold value.

During stimulation pulse 210F, channel 1 rate counter 206 causes a rate trigger, thereby causing $Q_1$ 208 to be incremented to a value of "2." At the termination of stimulation pulse 210F, $Q_2$ 218 is decremented to a value of "0" and the next pulse trigger 220M occurs. At pulse trigger 220M, stimulation generator 58 delivers stimulation pulse 200G on channel 1 because channel 1 has a backlog of pulses, as indicated by the value "2" in $Q_1$ 208, rate blanking interval 204F has expired, and channel 2 is rate blanking. Because $Q_T$ 219 has value of "3" at the clock cycle prior to pulse trigger 220M, stimulation generator 58 may shorten the recharge interval for stimulation waveform 200G within the predetermined limits. However, the recharge interval for channel 1 may already be adjusted to a minimum value in FIG. 6. Yet, because channels 1 and 2 are rate limit waiting, stimulation generator 58 may allow the recharge interval to extend past the predetermined interval, as shown in FIG. 6.

During stimulation pulse 200G, channel 2 rate counter 216 expires causing a rate trigger, thereby incrementing $Q_2$ 218 to a value of "1." When stimulation pulse 200G has been delivered, $Q_1$ 208 is decremented to a value of "1" and pulse trigger 220N occurs. However, rate blanking interval 214F has not yet expired when stimulation waveform 200G has been delivered. Rate blanking interval 204G also has not expired. Consequently, stimulation generator 58 cannot deliver a pulse on either channel 1 or channel 2. At the expiration of rate blanking interval 214F, stimulation generator 58 does not deliver stimulation on channel 2, even though channel 2 is available for delivering stimulation and has a backlog of pulses, because the value of $Q_1$ ("2") is greater than the value of $Q_2$ ("1") after waveform 200G expires. In other words, channel 1 has a backlog of pulses and needs to "catch up." This occurs because channel 1, which has a faster rate than channel 2, continues to build a backlog of pulses while waiting for channel 2 until the backlog of channel 1 is greater than that of channel 2. When the backlog of channel 1 is larger than that of channel 2, channel 1 delivers two consecutive pulses to "catch up" in order to maintain the programmed rate.

In FIG. 6, stimulation generator 58 delivers the next stimulation pulse, i.e., stimulation and recharge waveform 200H, when rate blanking interval 204G expires. Stimulation generator 58 waits while rate blanking interval 204G expires before delivering waveform 200H. The purpose of the rate blanking interval is described in greater detail below. Stimulation generator 58 also triggers rate blanking interval 204H and blanking timing 212H when waveform 200H is delivered. In accordance with the recharge rules, the recharge interval for waveform 200G remains unchanged because $Q_T$ 219 is "2" at the clock cycle prior to pulse trigger 220N. As previously described, the recharge interval for channel 1 may already be set to the minimal value. Thus, waveform 200H is illustrated as being approximately the same duration as waveform 200C in FIG. 6.

The purpose of rate blanking or a rate blanking interval is to prevent delivery of "adjacent" pulses on a single channel at an unnecessarily high rate. In this way, rate blanking provides separation between pulses on a channel, consistent with programmed amplitude with the allowance for a backlog of pulses. In some examples, the rate blanking interval may be adaptively adjusted. In such examples, the duration of the rate blanking interval may be adjusted based on the corresponding queue. In particular, the rate blanking interval may be decreased in situations where the recharge interval is set to the minimum value but stimulation generator 58 is still not able to "keep up." In other words, the rate blanking interval may be adjusted when a backlog of pulses increases by a predetermined amount. As an example, when the total queue $Q_T$ is less than 2, the rate blanking interval is not shortened. When $Q_T$ equals 2, the rate blanking interval is shortened by one clock cycle, e.g., about 3% of the rate blanking interval. When $Q_T$ exceeds 2, the rate blanking interval is shortened by two clock cycles, e.g., about 6% of the rate blanking interval.

The next pulse trigger, i.e., pulse trigger 220O, occurs when stimulation and recharge waveform 200H has completed. $Q_1$ 208 is decremented to a value of "1" due to the completion of delivery of waveform 200H. Stimulation generator 58 delivers stimulation pulse 210G on channel 2 in accordance with the stimulation rules, since $Q_2$ 218 equals $Q_1$ 208 but channel 1 106 is rate-limit-blanked. At some time after pulse trigger 220O, channel 2 rate counter 216 expires causing a rate trigger, thereby incrementing $Q_2$ 218 to a value of "2." Again, stimulation generator 58 does not decrease the recharge interval for stimulation waveform 210G, even though $Q_T$ 219 has a value of "3," since the recharge interval for channel 2 is already at the lower limit.

Figure 7:
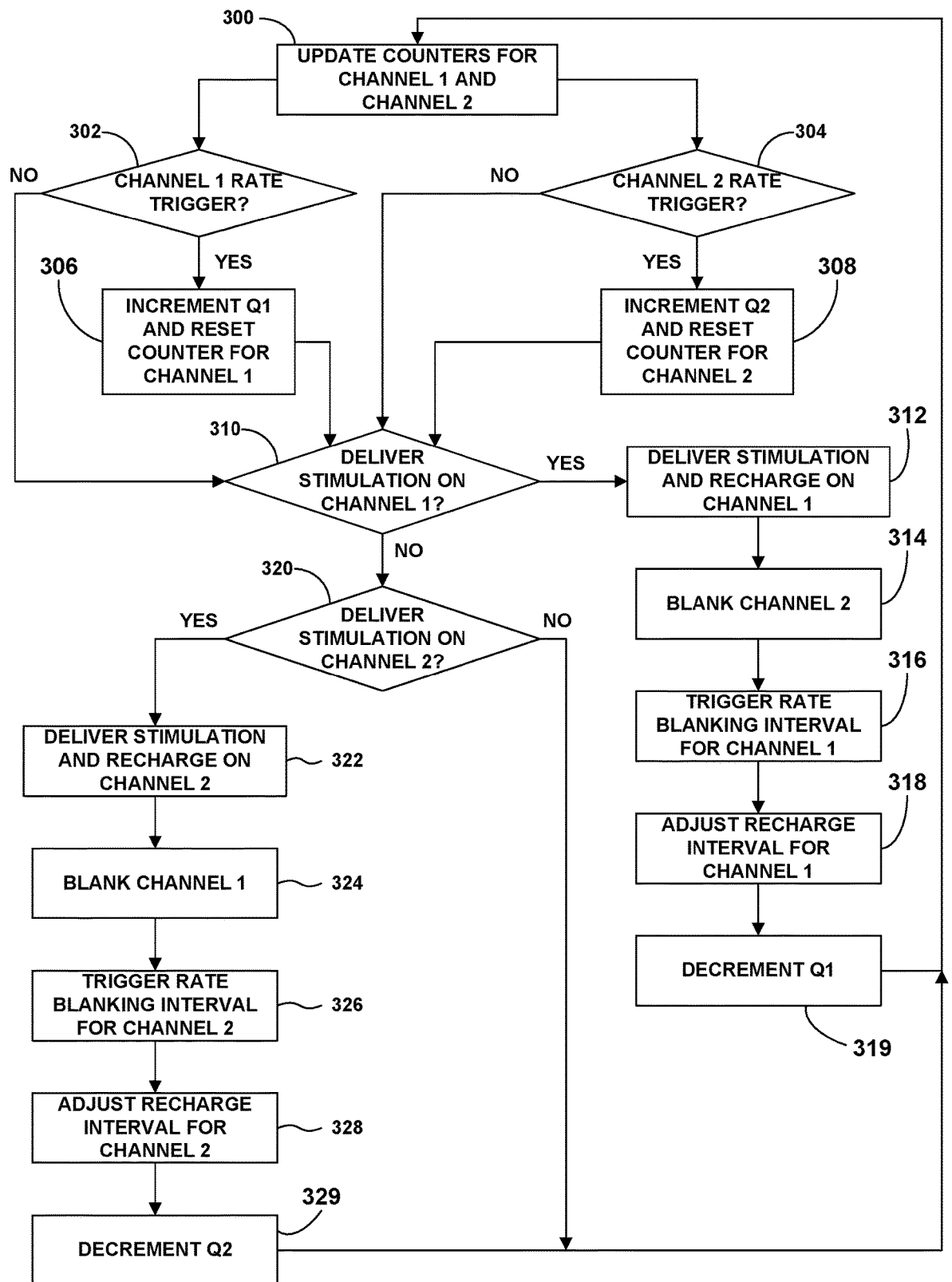
FIG. 7 is a flow diagram illustrating an example method that may be performed by the stimulator shown in FIG. 3 to deliver electrical stimulation to a patient at independent rates on different channels using a single stimulation generator.

FIG. 7 is a flow diagram illustrating an example method for adaptively delivering stimulation to patient 6 using a single stimulation generator over two or more independent channels so as to maintain the programmed rates, and adjusting recharge signals associated with the stimulation to provide a trade-off between fidelity to the programmed rates and amplitude sag or charge balance. The method shown in FIG. 7 provides a general description of the method used for delivering stimulation so as to maintain programmed rates and adaptively adjusting recharge signals for the stimulation. As previously described, stimulator 4 may perform these operations together or separately. For conciseness, these operations are shown together to illustrate how these operations can be performed together to provide the advantages described in this disclosure.

It should also be understood that the purpose of the flow diagram in FIG. 7 is to provide a general method for performing the techniques described in this disclosure. The steps in FIG. 7 are generally shown in a sequential order but, in some cases, one or more steps may be performed substantially simultaneously. For example, a processor may perform one or more steps in parallel. Steps which may be performed at substantially the same time may be indicated as such in this description. In some cases it should be understood that some steps provided in FIG. 7 may extend for a period of time and, thus, overlap with one or more following steps.

The first step in the example method shown in FIG. 7 is to update the counters for both channels (step 300), e.g., channel 1 rate counter 206 and channel 2 rate counter 216. As previously described, the counters may count up or count down to a value that corresponds to the programmed rate. For example, in FIG. 6, a value of 44 corresponds to a programmed rate of 182 Hz on channel 1, and a value of 48 corresponds to a programmed rate of 167 Hz on channel 2.

Stimulator 4 may then, concurrently or after the counters have begun counting, determine whether channel 1 counter 72 causes a rate trigger or channel 2 counter 73 causes a rate trigger (steps 302 and 304). Stimulator 4 may perform steps 302 and 304 at substantially the same time. When channel 1 counter 72 causes a rate trigger stimulator 4 may increment $Q_1$ 208 and reset channel 1 counter 72 (step 306). Similarly, stimulation 4 may increment $Q_2$ 218 and reset channel 2 counter 73 (step 308) when channel 2 counter 73 causes a rate trigger. Channel 1 counter 72 and channel 2 counter 73 cause a rate trigger when the counters count down to zero from a value corresponding to the programmed rate, or in some examples, count up to a value corresponding to the programmed rate.

After steps 302, 304, 306, and 308 are complete, stimulator 4 determines whether to deliver stimulation on channel 1 (step 310) or on channel 2 (step 320). As previously described, stimulator 4 determines on which channel to deliver stimulation based on $Q_1$ 208 and $Q_2$ 218 and, more particularly, in accordance with a set of stimulation rules stored in memory 52. An example flow diagram for performing steps 310 and 320 is provided in greater detail in FIG. 8.

However, with respect to the timing diagram shown in FIG. 7, stimulator 4 first determines whether to deliver stimulation on channel 1 (step 310). When stimulator 4 delivers stimulation on channel 1 ("YES" branch of decision block 310), stimulator 4 delivers stimulation and an associated recharge signal on channel 1 (step 312). In particular, stimulator 4 may first deliver an electrical stimulation pulse and then deliver a recharge signal after the electrical stimulation. As previously described, stimulator 4 may deliver the recharge signal through channel 1 to recover charge so that approximately zero net charge is delivered through channel 1 after the recharge signal has been delivered. Moreover, stimulator 4 may deliver the recharge signal in accordance with the recharge rules described in this disclosure. That is, stimulator 4 may, in some examples, deliver the recharge signal according to a recharge interval. The recharge interval may be adjusted according to the recharge rules. Stimulator 4 may also adjust the amplitude of the recharge signal as previously described in this disclosure. In other examples, stimulator 4 may deliver the recharge signal exceeding the programmed recharge interval, such as when the channels are rate limit waiting. In such examples, stimulator 4 may deliver the recharge signal for a time period longer than that specified by the recharge interval. Consequently, the step of delivering stimulation and an associated recharge signal on channel 1 in FIG. 7 (step 312) may also require determining whether the channels are rate limit waiting. If the channels are not rate limit waiting, stimulator 4 delivers the recharge signal according to specified parameters, i.e., recharge interval and recharge amplitude. If the channels are rate limit waiting, stimulator 4 delivers the recharge signal until the channels are not rate limit waiting. Stimulator 4 may determine if the channels are rate limit waiting based on the rate blanking intervals for the channels.

Stimulator 4 also blanks channel 2 (step 314) while delivering stimulation on channel 1 and triggers rate interval blanking for channel 1 (step 316). Although steps 314 and 316 are shown in FIG. 7 as sequential steps, stimulator 4 may execute steps 314 and 316 at the same time as step 312. However, it should be understood that steps 312, 314, and 316 may have different durations even though these steps may be initiated at the same time.

For example, stimulator 4 generally blanks channel 2 while delivering electrical stimulation and an associated recharge signal on channel 1. That is, stimulator 4 may deliver stimulation and a recharge signal on channel 1 over the same time period that stimulator 4 blanks channel 2. In contrast, stimulator 4 may trigger the rate blanking interval for channel 1 at approximately the same time it starts delivering the electrical stimulation on channel 1, but stimulator 4 may deliver the stimulation and recharge signal before the rate blanking interval ends.

In FIG. 7, stimulator 4 also adjusts the recharge interval for channel 1 (step 318). In some examples, stimulator 4 adjusts the recharge interval when stimulation and associated recharge signal has been delivered. Thus, stimulator 4 may adjust the recharge interval before the rate blanking interval has expired. Stimulator 4 adjusts the recharge interval in accordance with the previously described recharge rules. An example method for adjusting the recharge interval is provided in FIG. 9. Stimulator 4 may also decrement $Q_1$ 208 (step 319) when the stimulation and recharge signal has been delivered on channel 1 (step 319). Consequently, in some examples, stimulator 4 may perform steps 318 and 319 at approximately the same time.

When stimulator 4 determines to deliver stimulation on channel 2 ("YES" branch of decision block 320), stimulator 4 performs steps 322, 324, 326, 328, and 329 which are similar to steps 312, 314, 316, 318, and 319, respectively. With respect to FIG. 7, stimulator 4 delivers stimulation and an associated recharge signal on channel 2 according to the stimulation and recharge rules described in this disclosure (step 322), blanks channel 1 while delivering the electrical stimulation and recharge signal (step 324), and triggers a rate blanking interval for channel 2 (step 326). Again, stimulator 4 may begin executing steps 322, 324, and 326 at approximately the same time.

Stimulator 4 may then adjust the recharge interval for channel 2 (step 328) and decrement $Q_2$ 219 (step 329). Similar to steps 318 and 329, stimulator 4 may perform steps 328 and 329 at approximately the same time, i.e., when the stimulation and the associated recharge interval has been delivered on channel 2.

In the event that stimulator 4 does not deliver stimulation on either channel 1 or channel 2, stimulator 4 repeats the steps shown in FIG. 7. In this way, stimulator 4 recursively performs the illustrated steps as necessary.

Figure 8:
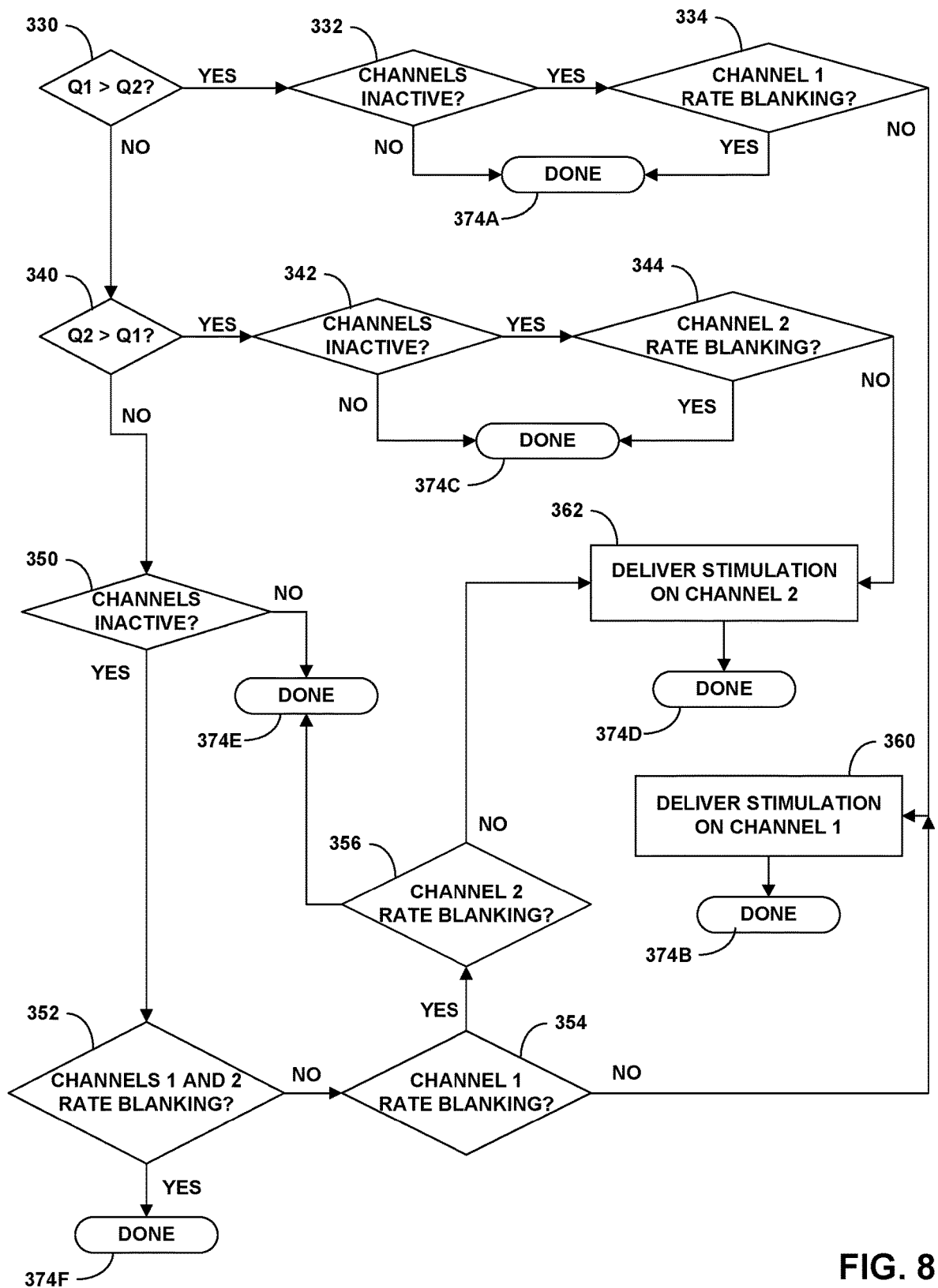
FIG. 8 is flow diagram illustrating in greater detail an example method for the delivery of stimulation on channels 1 and 2.

FIG. 8 is flow diagram illustrating in greater detail an example method for delivering stimulation on channels 1 and 2. The flow diagram of FIG. 8 depicts example steps that may be used to determine whether to deliver stimulation on channel 1 or channel 2 based on $Q_1$ 208 and $Q_2$ 218. In particular, the example illustrated in FIG. 8 may be viewed as a detailed method for performing the steps of 310 and 320 of the example method shown in FIG. 7. It should be understood that the purpose of the example method shown in FIG. 8 is to provide a conceptual view of the steps of the described method. Although the steps in FIG. 8 are shown in a sequential order, some of the steps may be performed in parallel within a processor and, thus, be executed at substantially the same time.

The first step of the example method illustrated in FIG. 8 is determining whether $Q_1$ 208 is larger than $Q_2$ 218 (step 330). When $Q_1$ 208 is larger than $Q_2$ 218, ("YES" branch of decision block 330) stimulator 4 will deliver stimulation on channel 1 if channel 1 is available for delivering stimulation. To determine if channel 1 is available for delivering stimulation, stimulator 4 determines whether the channels, i.e., channel 1 and channel 2, are inactive (step 332). As previously described, the channels are inactive when stimulation or recharge signals are not being delivered and the channels are not blanked. When both channels are inactive ("YES" branch of decision block 332), stimulator 4 determines whether channel 1 is rate blanking (step 334). If channel 1 is not rate blanking, stimulator 4 delivers stimulation on channel 1 (step 360) and the method ends (step 374B). If, however, one of channel 1 and channel 2 is active or if channel 1 is rate blanking the method ends (step 374A). When the method ends, as represented by the "done" block, stimulator 4 returns to the initial step of the example method illustrated in FIG. 7.

If $Q_1$ 208 is not larger than $Q_2$ 218 at step 330, stimulator 4 determines whether $Q_2$ 218 is larger than $Q_1$ 208 (step 340). If $Q_2$ 218 is larger than $Q_1$ 208, stimulator 4 will deliver stimulation on channel 2 if channel 2 is available for delivering stimulation. Stimulator 4 determines if channel 2 is available for delivering stimulation by performing steps similar to steps 332 and 334. For example, stimulator 4 determines whether both channels 1 and 2 are inactive (step 342) and, if both of channels 1 and 2 are inactive, stimulator 4 determines whether channel 2 is rate blanking (step 344). If channel 2 is not rate blanking, stimulator 4 delivers stimulation on channel 2 (step 362) and the method ends (374D). If, however, both of channels 1 and 2 are not inactive, or if channel 2 is rate blanking, stimulator 4 does not deliver stimulation and the method ends (step 374C).

In the event that the neither of steps 330 and 340 are satisfied, the queues for channel 1 and channel 2 are equal, i.e., $Q_1$ 208 and $Q_2$ 218 are equal. In this case, stimulator 4 delivers stimulation on whichever of channels 1 and 2 is available. That is, stimulator 4 delivers stimulation on the channel that is not rate blanking in this case.

In the flow diagram illustrated in FIG. 8, stimulator 4 determines if the channels are inactive (step 350). When one of the channels is active, the method is done (step 374E). If, however, the channels are inactive stimulator 4 determines if both of channels 1 and 2 are rate blanking (step 352). When both channels are rate blanking, the method is done (step 374F), and stimulator 4 may repeat the steps shown in FIG. 8.

If both the channels are not rate blanking, stimulator 4 determines if channel 1 is rate blanking (step 354). If channel 1 is not rate blanking, stimulator 4 delivers stimulation on channel 1 (step 360) and the method is done (step 374B). If channel 1 is rate blanking, stimulator 4 determines whether channel 2 is rate blanking (step 356). If channel 2 is not rate blanking, stimulator 4 delivers stimulation on channel 2 (step 362) and the method is done (374D). If channel 2 is rate blanking, then both channels 1 and 2 are rate blanking and the method ends (step 374E).

Figure 9:
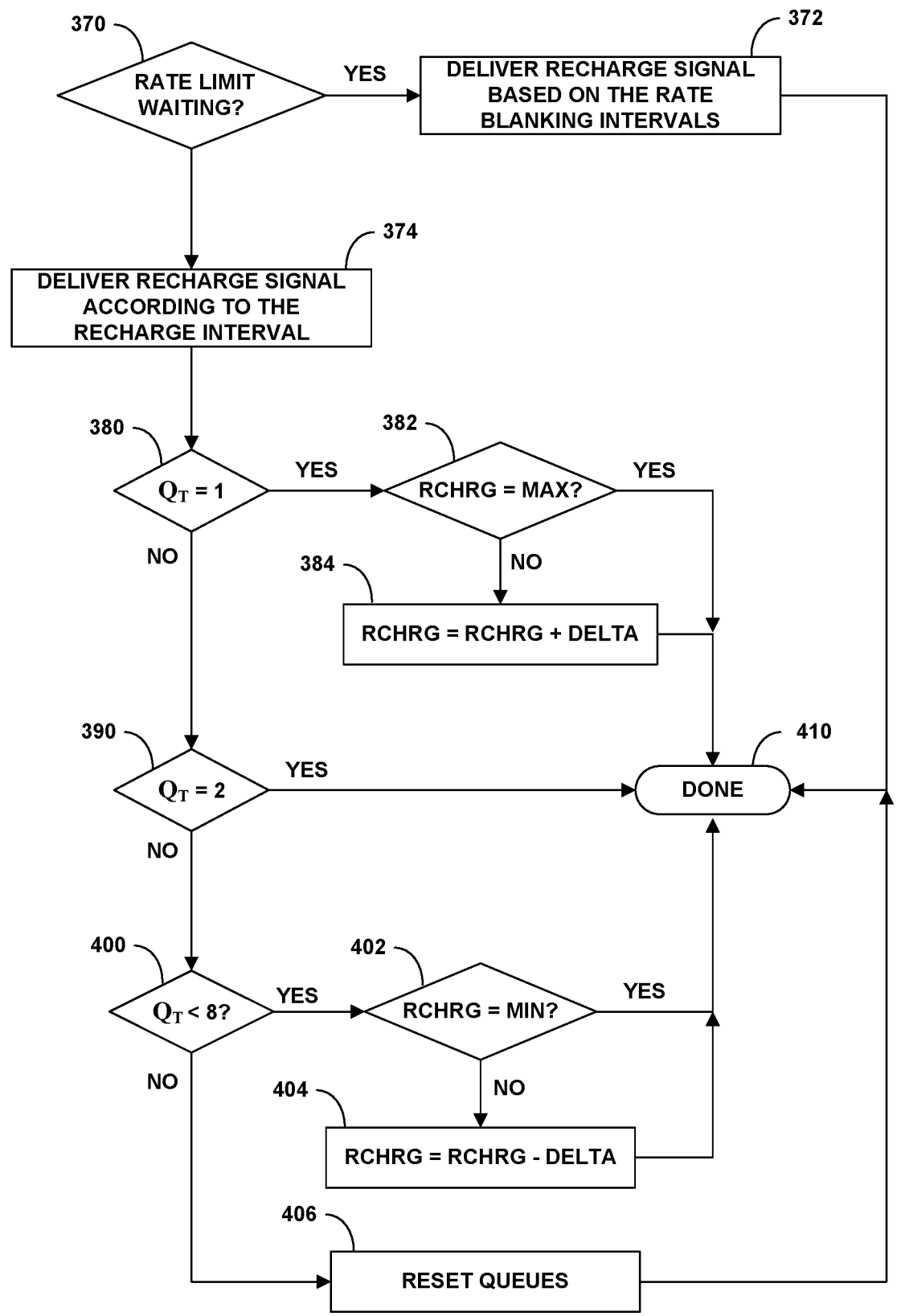
FIG. 9 is flow diagram illustrating in greater detail an example method for adjusting the recharge interval on channels 1 and 2.

FIG. 9 is flow diagram illustrating in greater detail an example method for adjusting the recharge interval on channels 1 and 2. Generally, the method illustrated in FIG. 9 provides example steps for increasing and decreasing the recharge intervals for two channels, channel 1 and channel 2, based on two queues, namely $Q_1$ 208 and $Q_2$ 218. In particular, the example illustrated in FIG. 9 may be viewed as a detailed method for performing either of steps 318 and 328 of FIG. 7. Accordingly, the steps of the example method illustrated in FIG. 9 are generic with respect to channel 1 and channel 2.

It should also be understood that the purpose of the example method shown in FIG. 9 is to provide a conceptual view of the steps of the described method. Although the steps in FIG. 9 are shown in a sequential order, some of the steps may be performed in parallel within a processor and, thus, be executed at substantially the same time.

The first step of the example method illustrated in FIG. 9 is determining whether the channels are rate limit waiting (step 370). Stimulator 4 may determine if the channels are wait limit waiting by examining channel 1 rate blanking counter 76 and channel 2 rate blanking counter 77 (FIG. 5). If rate blanking counters 76 and 77 have not expired, then the channels are rate limit waiting, and stimulator 4 delivers the recharge signal without regard to the predetermined recharge interval (step 372). Accordingly, stimulator 4 may deliver the recharge signal for a time period longer than the predetermined recharge interval. Stimulator 4 may not, however, deliver the recharge signal for a time period longer than the maximum allowed recharge interval. Thus, stimulator 4 may deliver the recharge signal until the charge balance is obtained, until the channels are no longer rate limit waiting, or until the maximum time period expires. Specifically, stimulator 4 may deliver the recharge signal until whichever of the previously listed events occurs first.

When the channels are not rate limit waiting, stimulator 4 delivers the recharge signal according to the recharge interval (step 374). As previously described, the recharge interval which stimulator 4 uses for delivering the recharge signal in step 374 is determined when the previous recharge signal had been delivered. Thus, when stimulator 4 has delivered the recharge signal in step 374, stimulator 4 performs the following steps shown in FIG. 9 to adjust the recharge interval for the next recharge signal.

In FIG. 9, stimulator 4 first determines if $Q_T$, is equal to "1," i.e., if the sum of the values of $Q_1$ 208 and $Q_2$ 218 is equal to "1" (step 380). When $Q_T$ is equal to "1," stimulator 4 determines whether the recharge interval for the channel, "RCHRG," is set to the maximum value, "MAX," (step 382). As previously described, the maximum value in some examples may be approximately 7.8 ms. If the recharge interval is not equal to the maximum value, stimulator 4 extends the recharge interval (step 384). In FIG. 9, stimulator 4 extends the recharge interval by a value "delta," where delta is a fixed predetermined amount, e.g., 1.95 ms, or a variable amount (step 384). The method ends (step 410) if the recharge interval had already been set to the maximum value ("YES" branch of decision block 382), or when stimulator 4 increases the recharge interval (step 384). When the method ends, stimulator 4 may repeat the steps of the example method illustrated in FIG. 7.

If $Q_T$ does not equal "1," then stimulator 4 may determine if $Q_T$ equals "2" (step 390). If $Q_T$ equals "2," the method ends (step 410) because stimulator 4 does not adjust the recharge interval. When $Q_T$ does not equal "2," stimulator 4 may then determine whether the value of $Q_T$ is less than 8 (step 400). If the value of $Q_T$ is not less than "8," stimulator 4 resets the queues, e.g., $Q_1$ 208 and $Q_2$ 218, (step 406). Resetting $Q_1$ 208 and $Q_2$ 218 may include setting $Q_1$ 208 and $Q_2$ 208 to zero. The purpose of resetting $Q_1$ 208 and $Q_2$ 218 is to prevent stimulator 4 from losing the "intelligence" for adjusting the recharge intervals. Although "8" is used as the value for determining when to reset the queues, other values may be used. In some examples, the value used to determine when to reset the queues may depend on the programmed rates. In any case, after stimulator 4 resets the queues, the method ends (step 410).

However, when the value of $Q_T$ is less than 8 (or other predetermined value), stimulator 4 determines whether the recharge interval for the channel is equal to the minimum value, "MIN," (step 402). On the other hand, if the recharge interval for the channel is not equal to the minimum value, stimulator 4 may decrease the recharge interval (step 404). As previously described, the minimum recharge interval may be approximately 1.95 ms. The method ends (step 410) if the recharge interval for the channel is equal to the minimum value, or when stimulator 4 decreases the recharge interval the method ends.

In the example method shown in FIG. 9, stimulator 4 decreases the recharge interval (RCHRG) by the value "delta." Thus, in the example shown in FIG. 9, stimulator 4 increases the recharge interval and decrease the recharge interval by the same amount. In other examples, however, stimulator 4 may increase and decrease the recharge interval by different amounts e.g., the value used for increasing the recharge interval may be different than the value used for decreasing the recharge interval. For example, stimulator 4 may decrease the recharge interval by a larger amount than stimulator 4 increases the recharge interval. As another example, stimulator 4 may adjust the recharge interval by selecting a value from a plurality of predefined values. As an example, the recharge interval may be selected to have a value of 7.8 ms, 5.9 ms, 4.9 ms, 3.9 ms, 2.9 ms, 1.9 ms, 1.5 ms, and 0.976 ms and stimulator 4 may increase the recharge interval by one of the predefined values.

Figure 10:
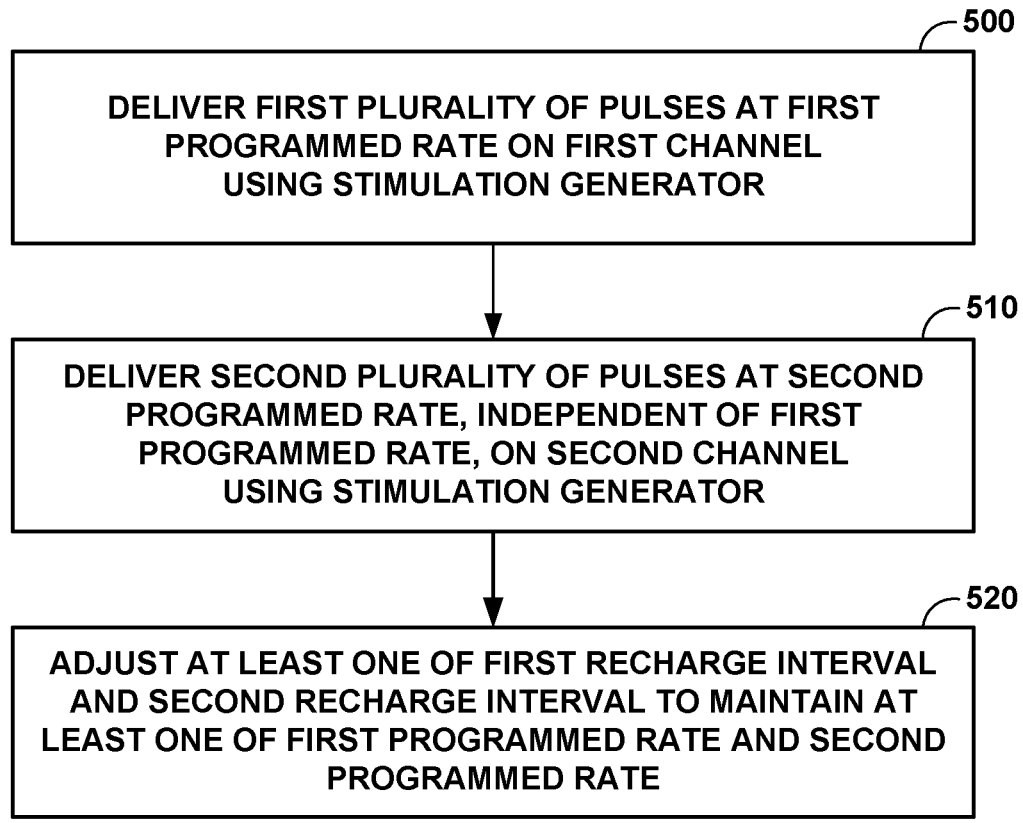
FIG. 10 is a flow diagram illustrating another example method that may be performed by the stimulator shown in FIG. 3 to deliver electrical stimulation to a patient at independent rates on different channels using a single stimulation generator.

FIG. 10 is a flow diagram illustrating another example method for adaptively delivering stimulation to patient 6 using a single stimulation generator over two or more independent channels so as to maintain the programmed rates, and adjusting recharge intervals associated with the stimulation to provide a trade-off between fidelity to the programmed rates and amplitude sag or charge balance. In FIG. 10, a first plurality of electrical stimulation pulses is delivered at a first programmed rate on a first channel using a stimulation generator (step 500). Then, a second plurality of electrical stimulation pulses is delivered at a second programmed rate on a second channel using the same stimulation generator that was used to deliver the first plurality of pulses (step 510). The second programmed rate is different than the first programmed rate, and the second programmed rate is independent of the first programmed rate. Independent rate control refers to the ability to control the electrical stimulation rate of each channel independently of the electrical stimulation rates of the other channels using the same stimulation generator. For example, in a two channel implementation independent rate control, the programmed stimulation rate of a second channel need not be a multiple of the programmed stimulation rate of the first channel. That is, the programmed rate on one channel is not restricted by the programmed rate on another channel. The method shown in FIG. 10 also includes the additional optional step of adjusting at least one of the first recharge interval and the second recharge interval in order to maintain at least one of the first programmed rate and the second programmed rate (step 520). That is, each of the first plurality of electrical stimulation pulses is associated with a first recharge pulse having a first recharge interval, and each of the second plurality of electrical stimulation pulses is associated with a second recharge pulse having a second recharge interval. According to the techniques of this disclosure, the recharge intervals may be adjusted in order to maintain the programmed rates of the first channel and the second channel. In some examples, adjusting comprises at least one of increasing by a predetermined amount and decreasing by a predetermined amount.

In other examples, the method shown in FIG. 10 may include providing a first queue associated with the first channel, e.g., channel 1 queue 74, providing a second queue associated with the second channel, e.g., channel 2 queue 75, and populating the first and second queues according to a set of rules, wherein adjusting the at least one of the first recharge interval and the second recharge interval is based at least partially on the population of the first and second queues. In one example, adjusting the at least one of the first recharge interval and the second recharge interval based at least partially on the population of the first and second queues comprises summing a value of the population of the first queue and a value of the population of the second queue, comparing the sum to at least one predetermined value, and determining whether to adjust the at least one of the first recharge interval and the second recharge interval based on the comparison.

In some examples, the method shown in FIG. 10 may include providing a first rate counter that counts downward and is associated with the first channel, e.g., channel 1 counter 72. The first rate counter may include an initial value that corresponds to the first programmed rate. The method may also include providing a second rate counter that counts downward and is associated with the second channel, e.g., channel 2 counter 73. The second rate counter may include an initial value that corresponds to the second programmed rate. Populating the first queue according to a set of rules may include incrementing a value of the population of the first queue when the first rate counter reaches zero and decrementing the value of the population of the first queue after each one of the first plurality of electrical stimulation pulses is delivered, and populating the second queue according to a set of rules may include incrementing a value of the population of the second queue when the second rate counter reaches zero and decrementing the value of the population of the second queue after each one of the second plurality of electrical stimulation pulses is delivered.

In one example, delivering the first plurality of electrical stimulation pulses at a first programmed rate on a first channel comprises, as shown in FIG. 10, may include preventing delivery of one of the second plurality of electrical stimulation pulses on the second channel, and delivering two consecutive electrical stimulation pulses on the first channel based at least partially on the population of the first and second queues in order to maintain the first programmed rate.

In another example, the method shown in FIG. 10 may include providing a first rate blanking counter associated with the first channel, e.g., channel 1 rate blanking counter 76, providing a second rate blanking counter associated with the second channel, e.g., channel 2 rate blanking counter 77, determining whether the first rate blanking counter has expired prior to delivering the first plurality of electrical stimulation pulses, and determining whether the second rate blanking counter has expired prior to delivering the second plurality of electrical stimulation pulses.

In one example, the method shown in FIG. 10 may include blanking, e.g., establishing a high impedance state across the corresponding electrodes, the second channel when delivering the first plurality of electrical stimulation pulses on the first channel, and blanking the first channel when delivering the second plurality of electrical stimulation pulses on the second channel.

In some examples, the electrical stimulation therapy delivered according to the method shown in FIG. 10, for example, is configured to treat at least one of chronic pain, tremor, Parkinson's disease, depression, epilepsy, urinary or fecal incontinence, pelvic pain, sexual dysfunction, obesity, migraines, and gastroparesis.

The techniques and components described in this disclosure may be implemented, at least in part, in hardware, software, firmware or any combination thereof. Electrical circuit components may be formed, for example, by integrated and/or discrete devices fabricated using any of a variety of conventional processes generally used for electrical circuitry provided in medical devices, such as implantable medical devices. Various control features may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. In this disclosure, the terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various embodiments of the invention have been described. These and other embodiments are within the scope of the following claims.

The invention claimed is:

1. A method for controlling delivery of electrical stimulation, the method comprising:
controlling a medical device to deliver a plurality of electrical stimulation signals, wherein each stimulation signal of the electrical stimulation signals is associated with a respective recharge signal having a default recharge interval;
adjusting, within a predefined interval limit that limits adjustment of the default recharge interval to an adjusted recharge interval, the default recharge interval of at least one recharge signal associated with one or more stimulation signals of the plurality of electrical stimulation signals to the adjusted recharge interval of the at least one recharge signal; and
controlling the medical device to deliver the at least one recharge signal at the adjusted recharge interval.

2. The method of claim 1, wherein the predefined interval limit comprises at least one of a maximum value or a minimum value.

3. The method of claim 1, wherein adjusting the default recharge interval of the at least one recharge signal comprises adjusting the default recharge interval by a fixed amount within the predefined interval limit.

4. The method of claim 1, wherein adjusting the default recharge interval of the at least one recharge signal comprises selecting the adjusted recharge interval from a plurality of recharge intervals that range between a maximum value and a minimum value of the predefined limit.

5. The method of claim 1, wherein adjusting the default recharge interval of the at least one recharge signal comprises reducing the default recharge interval to avoid delivery of the at least one recharge signal during delivery of a next electrical stimulation signal of the plurality of electrical stimulation signals.

6. The method of claim 1, wherein adjusting the default recharge interval of the at least one recharge signal comprises increasing the default recharge interval to balance charge from one or more electrical stimulation signals of the plurality of electrical stimulation signals.

7. The method of claim 1, wherein adjusting the default recharge interval of the at least one recharge signal comprises increasing the default recharge interval and reducing a recharge amplitude of the at least one recharge signal.

8. The method of claim 1, wherein the one or more electrical stimulation signals are a first one or more stimulation signals, and wherein the method further comprises adjusting an amplitude of at least one recharge signal associated with a second one or more stimulation signals of the plurality of electrical stimulation signals.

9. The method of claim 8, wherein adjusting the amplitude of the at least one recharge signal comprises adjusting the amplitude within an amplitude limit.

10. The method of claim 8, wherein adjusting the amplitude of the at least one recharge signal comprises increasing the amplitude of the at least one recharge signal when the recharge interval of the at least one recharge signal is shortened.

11. The method of claim 1, wherein:
controlling the medical device to deliver the plurality of electrical stimulation signals comprises controlling the medical device to deliver a first plurality of electrical stimulation signals at a first programmed rate on a first channel and controlling the medical device to deliver a second plurality of electrical stimulation signals at a second programmed rate on a second channel, the first programmed rate being different than the second programmed rate, and
adjusting the default recharge interval of the at least one recharge signal comprises adjusting the default recharge interval of the at least one recharge signal associated with one or more stimulation signals of at least one of the first plurality of electrical stimulation signals or the second plurality of electrical stimulation signals.

12. The method of claim 1, wherein the plurality of electrical stimulation signals comprises a plurality of electrical stimulation pulses, and wherein the respective recharge signal comprises a respective recharge pulse.

13. The method of claim 1, wherein the medical device comprises a stimulation generator configured to deliver the plurality of electrical stimulation signals and the respective recharge signal for each of the electrical stimulation signals.

14. A system for controlling delivery of electrical stimulation, the system comprising:
processing circuitry configured to:
control a medical device to deliver a plurality of electrical stimulation signals, wherein each stimulation signal of the electrical stimulation signals is associated with a respective recharge signal having a default recharge interval;
adjust, within a predefined interval limit that limits adjustment of the default recharge interval to an adjusted recharge interval, the default recharge interval of at least one recharge signal associated with one or more stimulation signals of the plurality of electrical stimulation signals to the adjusted recharge interval of the at least one recharge signal; and control the medical device to deliver the at least one recharge signal at the adjusted recharge interval.

15. The system of claim 14, wherein the predefined interval limit comprises at least one of a maximum value or a minimum value.

16. The system of claim 14, wherein the processing circuitry is configured to adjust the default recharge interval of the at least one recharge signal by at least adjusting the default recharge interval by a fixed amount within the predefined interval limit.

17. The system of claim 14, wherein the processing circuitry is configured to adjust the default recharge interval of the at least one recharge signal by at least selecting the adjusted recharge interval from a plurality of recharge intervals that range between a maximum value and a minimum value of the predefined limit.

18. The system of claim 14, wherein the processing circuitry is configured to adjust the default recharge interval of the at least one recharge signal by at least reducing the default recharge interval to avoid delivery of the at least one recharge signal during delivery of a next electrical stimulation signal of the plurality of electrical stimulation signals.

19. The system of claim 14, wherein the processing circuitry is configured to adjust the default recharge interval of the at least one recharge signal by at least increasing the default recharge interval to balance charge from one or more electrical stimulation signals of the plurality of electrical stimulation signals.

20. The system of claim 14, wherein the processing circuitry is configured to adjust the default recharge interval of the at least one recharge signal by at least increasing the default recharge interval and reducing a recharge amplitude of the at least one recharge signal.

21. The system of claim 14, wherein the one or more electrical stimulation signals are a first one or more stimulation signals, and wherein the processing circuitry is configured to adjust an amplitude of at least one recharge signal associated with a second one or more stimulation signals of the plurality of electrical stimulation signals.

22. The system of claim 21, wherein the processing circuitry is configured to adjust the amplitude of the at least one recharge signal by at least adjusting the amplitude within an amplitude limit.

23. The system of claim 21, wherein the processing circuitry is configured to adjust the amplitude of the at least one recharge signal by at least increasing the amplitude of the at least one recharge signal when the recharge interval of the at least one recharge signal is shortened.

24. The system of claim 14, wherein the processing circuitry is configured to:
control the medical device to deliver the plurality of electrical stimulation signals by at least controlling the medical device to deliver a first plurality of electrical stimulation signals at a first programmed rate on a first channel and controlling the medical device to deliver a second plurality of electrical stimulation signals at a second programmed rate on a second channel, the first programmed rate being different than the second programmed rate, and
adjust the default recharge interval of the at least one recharge signal by at least adjusting the default recharge interval of the at least one recharge signal associated with one or more stimulation signals of at least one of the first plurality of electrical stimulation signals or the second plurality of electrical stimulation signals.

25. The system of claim 14, wherein the plurality of electrical stimulation signals comprises a plurality of electrical stimulation pulses, and wherein the respective recharge signal comprises a respective recharge pulse.

26. The system of claim 14, further comprising a stimulation generator configured to deliver the plurality of electrical stimulation signals and the respective recharge signal for each of the electrical stimulation signals, wherein the medical device comprises the stimulation generator.

27. An implantable medical device comprising:
a stimulation generator configured to deliver a plurality of electrical stimulation signals, wherein each stimulation signal of the electrical stimulation signals is associated with a respective recharge signal having a default recharge interval; and
processing circuitry configured to:
control the stimulation generator to deliver the plurality of electrical stimulation signals;
adjust, within a predefined interval limit that limits adjustment of the default recharge interval to an adjusted recharge interval, the default recharge interval of at least one recharge signal associated with one or more stimulation signals of the plurality of electrical stimulation signals to the adjusted recharge interval of the at least one recharge signal; and
control the stimulation generator to deliver the at least one recharge signal at the adjusted recharge interval.

* * * * *